United States Patent
Berkowitz et al.

(10) Patent No.: US 11,685,724 B2
(45) Date of Patent: Jun. 27, 2023

(54) SYNTHETIC INTERMEDIATES FOR NOVEL CANNABINOIDS AND CANNABINOID ACIDS AND THEIR DERIVATIVES

(71) Applicant: Bessor Pharma, LLC, Framingham, MA (US)

(72) Inventors: Barry A. Berkowitz, Framingham, MA (US); Anthony G. Barrett, Rio de Janeiro (BR); Daniel Elliott, Basel (CH)

(73) Assignee: Bessor Pharma, LLC, Framingham, MA (US)

( * ) Notice: Subject to any disclaimer, the term of this patent is extended or adjusted under 35 U.S.C. 154(b) by 0 days.

(21) Appl. No.: 17/738,055

(22) Filed: May 6, 2022

(65) Prior Publication Data
US 2022/0340537 A1 Oct. 27, 2022

Related U.S. Application Data

(62) Division of application No. 17/269,732, filed as application No. PCT/US2019/047280 on Aug. 20, 2019, now Pat. No. 11,370,768.
(Continued)

(51) Int. Cl.
*C07D 319/06* (2006.01)
*C07D 311/78* (2006.01)
(Continued)

(52) U.S. Cl.
CPC ............ *C07D 311/78* (2013.01); *A61K 31/05* (2013.01); *A61K 31/352* (2013.01); *C07C 37/50* (2013.01);
(Continued)

(58) Field of Classification Search
None
See application file for complete search history.

(56) References Cited

U.S. PATENT DOCUMENTS

| | | |
|---|---|---|
| 2007/0213369 A1 | 9/2007 | Garzon et al. |
| 2017/0008869 A1 | 1/2017 | Dialer et al. |
| 2018/0170846 A1 | 6/2018 | McAllister et al. |

OTHER PUBLICATIONS

International Search Report and Written Opinion dated Dec. 13, 2019 for International Patent Application No. PCT/US2019/047280.

(Continued)

Primary Examiner — Samantha L Shterengarts
(74) Attorney, Agent, or Firm — Alix, Yale & Ristas, LLP

(57) ABSTRACT

The present invention relates to intermediate compounds for the synthesis of novel cannabinoids 1 and 2, synthesized from simple starting materials using a cascade sequence of allylic rearrangement, aromatization and, for tetracyclic cannabinoids, further highly stereoselective and regioselective cyclization. These synthesized cannabinoids can more easily be obtained at high purity levels than cannabinoids isolated or synthesized via known methods. The cannabinoids 2 are obtained containing very low levels of isomeric cannabinoids such as the undesirable $\Delta^8$-tetrahydrocannabinol. The analogues with variation in aromatic ring substituents, whilst easily synthesized with the new methodology, would be much more difficult to make from any of the components of cannabis oil.

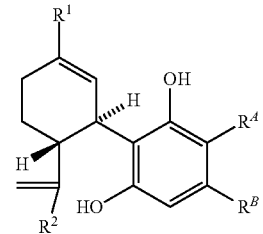

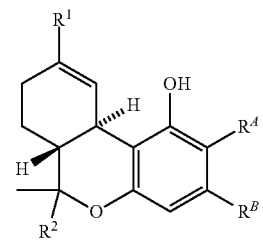

Novel compounds of the formulas 3 and 6, useful as intermediates for the synthesis of the cannabinoids of advanced intermediates 4 and 5 as well as cannabinoids of the formulas 1 and 2, are disclosed.

(Continued)

-continued

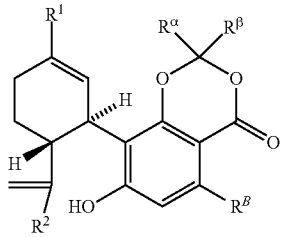

4

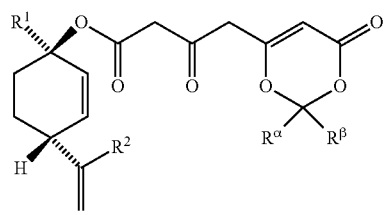

6

19 Claims, 2 Drawing Sheets

5

Related U.S. Application Data

(60) Provisional application No. 62/719,813, filed on Aug. 20, 2018.

(51) Int. Cl.
    *C07C 39/23*      (2006.01)
    *C07D 319/08*    (2006.01)
    *C07D 493/04*    (2006.01)
    *A61K 31/05*     (2006.01)
    *A61K 31/352*    (2006.01)
    *C07C 37/50*     (2006.01)
    *C07C 37/56*     (2006.01)

(52) U.S. Cl.
    CPC .............. *C07C 37/56* (2013.01); *C07C 39/23* (2013.01); *C07D 319/08* (2013.01); *C07D 493/04* (2013.01); *C07C 2601/16* (2017.05)

(56) References Cited

OTHER PUBLICATIONS

"2-[(6R)-3-(Hydroxymethyl)-6-prop-1-en-2-ylcyclohex-2-en-1-yl]-5-pentylbenzene-1,3-diol," Compound Summary, PubChem CID 9862348, Oct. 25, 2006.
"6a,7,8,10a-Tetrahydro-1-hydroxy-6,6-dimethyl-3-pentyl-6H-dibenzo(b,d)pyran-9-methanol," Compound Summary, PubChem CID 37482, Mar. 28, 2005.

SYNTHETIC INTERMEDIATES FOR NOVEL CANNABINOIDS AND CANNABINOID ACIDS AND THEIR DERIVATIVES

FIELD OF THE INVENTION

The field of the invention relates to methods for the synthesis of high purity known and novel cannabinoids including but not limited to $\Delta^9$-tetrahydrocannabinol (7), tetrahydrocannabivarin (9), cannabidiol (11), cannabidivarin (12) and other naturally occurring cannabinoids and other synthetic analogues from simple inexpensive starting materials by construction of the aromatic core. The field of the invention additionally covers novel cannabinoids, which may be used as active compounds either alone or admixed in combination with known cannabinoids and/or other drugs in drug formulations for the treatment of pain, multiple sclerosis-related spasticity, nausea, anorexia, epilepsy, Alzheimer's and neurodegenerative diseases, brain injury/concussion/traumatic brain injury, stroke, cancer, reduction of inflammation and immuno-inflammation related diseases, diseases/injury of the eye including but not limited to glaucoma, dry eye, corneal injury or disease and retinal degeneration or disease, disorders of immune-inflammation, lung injury or disease, liver injury or disease, kidney injury or disease, pancreatitis and disorders of the pancreas cardiovascular injury or disease, and organ transplant, reduction of post-surgical inflammation among other diseases, anti-oxidants and indications

BACKGROUND OF THE INVENTION

*Cannabis* ("marijuana") is a plant of considerable notoriety and use particularly for the species *Cannabis sativa*. Marijuana use as a recreational drug worldwide, has been and remains the subject of high interest and legal review in many countries of the world. There has been very considerable interest in the use of this plant and its extracts as ethnopharmaceuticals for millennia with reference even in Herodotus, (The Histories, Book IV, page 295, Penguin Books, Ltd., Middlesex (1972). The plant and its extracts have been and are used in medicine on account of their effects including as hypnotic agents, anti-anxiety agents, inflammation and immuno-inflammation regulatory agents, on pain including cancer pain, pain, neuropathic pain, spasmolytics, to combat the side effects of cancer chemotherapy including nausea, in the treatment of glaucoma, epilepsy and as appetite stimulant including for AIDS patients among other users.

There are over 60 constituent compounds that have been isolated and characterized from *Cannabis sativa* oil (for example see S. A. Ahmed, S. A. Ross, D. Slade, M. M. Radwan, F. Zulfiqar and M. A. ElSohly "Cannabinoid Ester Constituents from High-Potency *Cannabis sativa*", *Journal of Natural Products,* 2008, volume 71, pages 536-542 and references therein). In addition, a considerable number of these natural products and analogs have been prepared by total synthesis from aromatic and monoterpene precursor compounds. Such total syntheses are reported (for examples see R. K. Razdan, "The Total Synthesis of Cannabinoids" in "*The Total Synthesis of Natural Products*", Editor J. ApSimon, 1996, volume 4, pages 185-262, New York, N.Y.: Wiley and Sons; J. W. Huffman and J. A. H. Lainton, "Recent Developments in the Medicinal Chemistry of Cannabinoids", *Current Medicinal Chemistry,* 1996, volume 3, pages 101-116; N. Itagaki, T. Sugahara and Y. Iwabuchi, "Expedient Synthesis of Potent Cannabinoid Receptor Agonist (−)-CP55,940", *Organic Letters,* 2005, volume 7, pages 4181-4183; J. A. Teske and A. Deiters, "A Cyclotrimerization Route to Cannabinoids", *Organic Letters,* 2008, volume 10, pages 2195-2198; S. Tchilibon and R. Mechoulam, "Synthesis of a Primary Metabolite of Cannabidiol", *Organic Letters,* 2000, volume 2, pages 3301-3303; Y. Song, S. Hwang, P. Gong, D. Kim and S. Kim*, "Stereoselective Total Synthesis of (−)-Perrottetinene and Assignment of Its Absolute Configuration", *Organic Letters,* 2008, volume 10, pages 269-271; Y. Kobayashi, A. Takeuchi and Y.-G. Wang, "Synthesis of Cannabidiols via Alkenylation of Cyclohexenyl Monoacetate", *Organic Letters,* 2006, volume 8, pages 2699-2702; B. M. Trost and K. Dogra, "Synthesis of (−)-$\Delta^9$-trans-Tetrahydrocannabinol: Stereocontrol via Mo-Catalyzed Asymmetric Allylic Alkylation Reaction", *Organic Letters,* 2007, volume 9, pages 861-863; L.-J. Cheng, J.-H. Xie, Y. Chen, L.-X. Wang and Q.-L. Zhou, "Enantioselective Total Synthesis of (−)-$\Delta^8$-THC and (−)-$\Delta^9$-THC via Catalytic Asymmetric Hydrogenation and $S_NAr$ Cyclization" *Organic Letters,* 2013, volume 15, pages 764-767; P. R. Nandaluru and G. J. Bodwell, "Multicomponent Synthesis of 6H-Dibenzo[b,d]pyran-6-ones and a Total Synthesis of Cannabinol", *Organic Letters,* 2012, volume 14, pages 310-313; S. Ben-Shabat, L. O. Hanus, G. Katzavian and R. Gallily, "New Cannabidiol Derivatives: Synthesis, Binding to Cannabinoid Receptor, and Evaluation of Their Antiinflammatory Activity", *Journal of Medicinal Chemistry,* 2006, volume 49, pages 1113-1117; A. Mahadevan, C. Siegel, B. R. Martin, M. E. Abood, I. Beletskaya and R. K. Razdan, "Novel Cannabinol Probes for CB1 and CB2 Cannabinoid Receptors", *Journal of Medicinal Chemistry,* 2000, volume 43, pages 3778-3785; S. P. Nikas, S. O. Alapafuja, I. Papanastasiou, C. A. Paronis, V. G. Shukla, D. P. Papahatjis, A. L. Bowman, A. Halikhedkar, X. Han and A. Makriyannis, "Novel 1',1'-Chain Substituted Hexahydrocannabinols: 9β-Hydroxy-3-(1-hexyl-cyclobut-1-yl)-hexahydrocannabinol (AM2389) a Highly Potent Cannabinoid Receptor 1 (CB1) Agonist", *Journal of Medicinal Chemistry,* 2010, volume 53, pages 6996-7010).

In the last twenty years it has become apparent that the cannabinoids are in a renaissance for diverse biomedical uses. The pharmacology of the cannabinoids has been shown to be associated with a number of receptors and mechanisms including cannabinoids receptors, GPCR receptors, serotonin receptors, modulation of several voltage-gated channels (including $Ca^{2+}$, $Na_+$, and various type of $K^+$ channels), ligand-gated ion channels (i.e., GABA, glycine and TRPV), Toll like receptors, opioid receptors, NMDA or excitatory amino acids receptors, catecholamine receptors, enzymes regulating endocannabinoids, and ion-transporting membranes proteins such as transient potential receptor class (TRP) channels (L. De Petrocellis, M. Nabissi, G. Santoni and A. Ligresti, "Actions and Regulation of Ionotropic Cannabinoid Receptors", Advances in Pharmacology, 2017, volume 80, pages 249-289; P. Morales and P. H. Reggio, "An Update on Non-$CB_1$, Non-$CB_2$ Cannabinoid Related G-Protein-Coupled Receptors", Cannabis Cannabinoid Research, 2017, volume 2, pages 265-273). Thus, it would be helpful to have a new medicament or medicaments that include one or more cannabinoids for treatment of afflictions known to be treatable by affecting or using these physiological mechanisms.

Much of the work with cannabinoids have considered that its actions are for a number of indications includes directly or indirectly receptor-mediated effects by two G protein-coupled receptors, named $CB_1$ and $CB_2$, which have 44% sequence homology in humans. The $CB_1$ sub-type is the most widely expressed G protein-coupled receptor in the brain in regions, for example, that control motor, emotional, cognitive, sensory responses, perception of pain, thermoregulation, as well as cardiovascular, gastrointestinal, and respiratory physiology. It is localized in the central (CNS) and peripheral nervous systems including the olfactory bulb, cortical areas, parts of the basal ganglia, thalamus, hypothalamus, cerebellar cortex, brainstem, and spinal cord. $CB_1$ receptors also occur in cells in the pituitary and thyroid glands, some fat, muscle and liver cells as well as the lung and kidneys. The $CB_2$ sub-type is expressed in immune and hematopoietic cells, osteoclasts, and osteoblasts and mediates the response of the immune system, controls inflammation, modulates inflammatory and neuropathic pain as well as bone remodeling. Thus, it would be helpful to have a new medicament or medicaments for treatment of afflictions known to be treatable by affecting these physiological paths that includes one or more cannabinoids for preventing, treating or curing inflammatory mediated diseases or inflammatory mediated pathological conditions of one or more from the group consisting of the central or peripheral nervous system, cardiovascular-renal system, skin, gastrointestinal system, pulmonary-respiratory system, endocrine system, joints, musculo-skeletal system, blood or lymph system, genitourinary system, eye, and ear or for the prevention, treatment or cure of one or more anorexia, arthritis, cancer, pain, glaucoma, migraine, persistent muscle spasms in an individual or animal in need of treatment and seizures.

The pharmacology of modulators of $CB_1$ and $CB_2$ receptors has been reviewed for example by Vemuri and Makriyannis (V. K. Vemuri and A. Makriyannis, "Medicinal Chemistry of Cannabinoids", Clinical Pharmacology & Therapeutics, 2015, volume 97, pages 553-558). The psychoactive effects of $\Delta^9$-tetrahydrocannabinol (7) as well as with its primary metabolite 11-hydroxy-$\Delta^9$-tetrahydrocannabinol (8) are mediated by its partial agonism of CNS $CB_1$ receptors (J. van Amsterdam, T. Brunt and W. van den Brink, "The adverse health effects of synthetic cannabinoids with emphasis on psychosis-like effects", Journal of Psychopharmacology, 2015, volume 29, pages 254-263; R. G. Pertwee, "The diverse $CB_1$ and $CB_2$ receptor pharmacology of three plant cannabinoids: $\Delta^9$-tetrahydrocannabinol, cannabidiol and $\Delta^9$-tetrahydrocannabivarin", British Journal of Pharmacology, 2008, volume 153, pages 199-215). It is useful as an analgesic, an antiemetic agent, and for treating anorexia in patients with AIDS. Other $CB_1$ receptor modulators include tetrahydrocannabivarin (9) (weak antagonist) and cannabinol (10) (weak agonist) and both are modest agonists of $CB_2$. Both the non-psychoactive (−)-cannabidiol (11) and cannabidivarin (12) do not interact significantly with either receptor sub-class and their modes of action are less clear (J. Fernández-Ruiz, O. Sagredo, M. R. Pazos, C. García, R. Pertwee, R. Mechoulam, J. Martínez-Orgado, "Cannabidiol for neurodegenerative disorders: important new clinical applications for this phytocannabinoid?", British Journal of Clinical Pharmacology, 2013, volume 75, pages 323-333; S. Rosenthaler, B. Pöhn, C. Kolmanz, C. N. Huu, C. Krewenka, A. Huber, B. Kranner, W.-D. Rausch and R. Moldzio, "Differences in receptor binding affinity of several phytocannabinoids do not explain their effects on neural cell cultures", Neurotoxicology and Teratology, 2014, volume 46, pages 49-56). The combination of $\Delta^9$-tetrahydrocannabinol (7) and cannabidiol (11) (Sativex, Nabiximols) is used to treat multiple sclerosis-related spasticity and as a potent analgesic in patients with advanced stage cancers. More recently, purified cannabidiol (11) was granted orphan drug status for treating epilepsy. $CB_1$ receptor antagonists are appetite suppressants, enhance cognition, and control addictive behavior. Selective $CB_2$ agonists may provide superior analgesic agents and immunomodulators that do not have the undesirable psychoactive effects associated with CNS $CB_1$ agonism. $\Delta^9$-Tetrahydrocannabinol (7) (Dronabinol) has been shown to be clinically effective either in monotherapy or in combination with ondansetron (Zofran, a 5-$HT_3$ antagonists) and in combination with prochlorperazine (a dopamine $D_2$ receptor antagonist) to treat chemotherapy-induced nausea and vomiting in cancer patients (M. B. May and A. E Glode, "Dronabinol for chemotherapy-induced nausea and vomiting unresponsive to antiemetics", Cancer Management and Research, 2016, volume 8, pages 49-55).

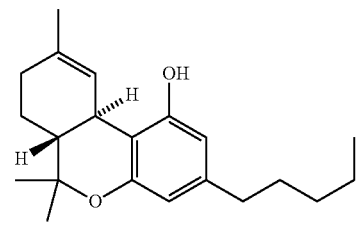

Tetrahydrocannabinol (7)

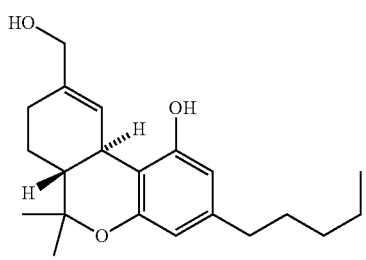

11-Hydroxytetrahydrocannabinol (8)

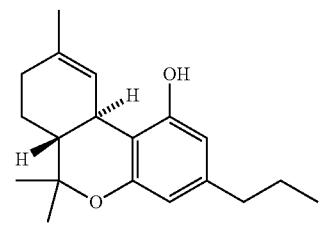

Tetrahydrocannabivarin (9)

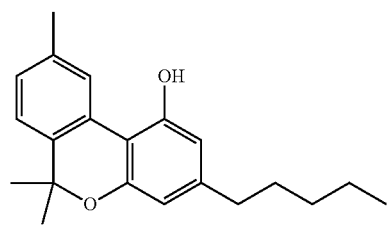

Cannabinol (10)

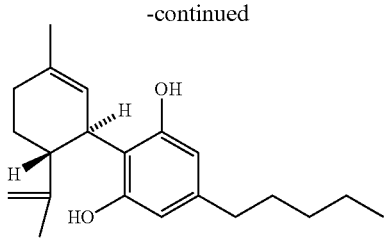

Cannabidiol (11)

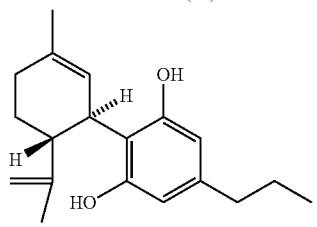

Cannabidivarin (12)

Cannabinoids that are used as therapeutics are currently either obtained from the fractionation of cannabis or cannabis oil or from total synthesis usually from aromatic and terpene starting materials. Since there are over 60 different natural products in cannabis and its oil, such fractionation requires extensive chromatographic purification to provide any individual constituent substantially pure and with so many components makes reproducible production and storage difficult. In the context of this patent application, substantially pure means at least 99% chemically (constitutionally, diastereoisomerically and enantiomerically) pure and additionally not contaminated with any agrochemicals including herbicides, fungicides and insecticides or any pathogens that may be associated with cannabinoids isolated from plant-derived cannabis oil. The purification of $\Delta^9$-tetrahydrocannabinol (7) from other cannabis constituents but particularly from its isomer $\Delta^8$-tetrahydrocannabinol is inefficient and costly. In addition, since many of the cannabinoids in cannabis oil have different effects as total, partial, inverse or neutral agonists or antagonists of either or both of the $CB_1$ and $CB_2$ receptors, it is especially important that individual isolated natural products do not contain significant levels (below parts per million levels) of any other cannabinoid natural product, which has undesired biological effects and that the specifications set are efficiently reproducible. There is an added complication in that many cannabinoid natural products are obtained as oils, which are typically not possible to crystallize and which are prone to air oxidative degradation and their isolation requires the use of extensive expensive and difficult to scale chromatography and/or derivatisation (for example see B. Trawick and M. H. Owens, "Process for the Preparation of (−)-delta 9-Tetrahydrocannabinol", WO 2009/099868 A1; E. Arslantas and U. Weigl, "Method for Obtaining Pure Tetrahydrocannabinol", U.S. Pat. No. 7,923,558 B2; J. E. Field, J. Oudenes, B. I. Gorin, R. Orprecio, F. E. Silva e Souza, N. J. Ramjit and E.-L. Moore, "Separation of Tetrahydrocannabinols", U.S. Pat. No. 7,321,047 B2; P. Bhatarah, K. J. Batchelor, D. McHattie and A. K. Greenwood, "Delta 9 Tetrahydrocannabinol Derivatives", WO 2008/099183 A1; D. C. Burdick, S. J. Collier, F. Jos, B. Biolatto, B. J. Paul, H. Meckler, M. A. Helle and A. J. Habershaw, "Process for Production of Delta-9-Tetrahydrocannabinol", U.S. Pat. No. 7,674,922 B2). Secondly, many synthetic routes to prepare cannabinoids either use expensive reagents and are uneconomic to use on a large scale or are dependent on the condensation reactions of monoterpene starting materials with derivatives of alkyl-resorcinol such as 5-n-pentyl-resorcinol (olivetol) under acidic reaction conditions, reactions that frequently give rise to side products derived from carbenium ion rearrangement reactions and/or side reactions. For example, the manufacture of $\Delta^9$-tetrahydrocannabinol (7) from olivetol and monoterpenes by Brønsted or Lewis acid catalyzed condensation reactions is complicated by the co-formation of its isomer $\Delta^8$-tetrahydrocannabinol, amongst other impurities. Such impurities also considerably complicate and increase the cost of obtaining cannabinoid active pharmaceutical ingredients substantially pure (for examples see R. K. Razdan, "The Total Synthesis of Cannabinoids" in "The Total Synthesis of Natural Products", Editor J. ApSimon, 1996, volume 4, pages 185-262, New York, N.Y.: Wiley and Sons; C. Steup and T. Herkenroth, "Process for Preparing Synthetic Cannabinoids", US Patent Application 2010/0298579 A1; R. J. Kupper, "Cannabinoid Active Pharmaceutical Ingredient for Improved Dosage Forms", WO 2006/133941 A2; J. Erler, and S. Heitner, "Method for the Preparation of Dronabinol", U.S. Pat. No. 8,324,408 B2; A. L. Gutman, M. Etinger, I. Fedotev, R. Khanolkar, G. A. Nisnevich, B. Pertsikov, I. Rukhman and B. Tishin, "Methods for Purifying trans-(−)-$\Delta^9$-Tetrahydrocannabinol and trans-(+)-$\Delta^9$-Tetrahydrocannabinol", U.S. Pat. No. 9,278,083 B2). The present invention is directed towards overcoming these problems and, as well as providing efficient/reproducible manufacturing routes for known cannabinoids, provides flexible syntheses of novel cannabinoids, which may be used as active compounds either alone or admixed in combination with known cannabinoids and/or other drugs in drug formulations for the treatment of pain, multiple sclerosis-related spasticity, nausea, epilepsy, Alzheimer's brain injury/concussion, cancer, immune-inflammation mediated disorders, amongst other pathologies.

SUMMARY OF THE INVENTION

Among the benefits and improvements disclosed herein, other objects and advantages of the disclosed embodiments will become apparent from the following wherein like numerals represent like parts throughout the several figures. Detailed embodiments of cannabinoid compounds, intermediary compounds, and a process for preparation of cannabinoid and cannabimimetic compounds and their intermediaries are disclosed; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "In some embodiments" and "in some embodiments" as used herein do not necessarily refer to the same embodiment(s), though it may. The phrases "in another embodiment" and "in some other embodiments" as used herein do not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on"

is not exclusive and allows for being based on additional factors not described, unless the context clearly dictates otherwise. In addition, throughout the specification, the meaning of "a," "an," and "the" include plural references. The meaning of "in" includes "in" and "on".

Further, the terms "substantial," "substantially," "similar," "similarly," "analogous," "analogously," "approximate," "approximately," and any combination thereof mean that differences between compared features or characteristics is less than 25% of the respective values/magnitudes in which the compared features or characteristics are measured and/or defined.

As used herein, the term "substituted benzyl" means a benzyl ring bearing 1, 2 or 3 independently varied C1-C4 alkyl, C1-C4 alkyloxy, fluoro, chloro, hydroxy, trifluoromethyl, trifluoromethoxy, methylenedioxy, cyano, or methoxymethyl groups at an aromatic ring position or 1 or 2 independently varied C1-C4 alkyl at the benzylic methylene.

As used herein, the term "optionally substituted aryl" means a phenyl ring optionally bearing 1, 2 or 3 independently varied C1-C4 alkyl, C1-C4 alkyloxy, fluoro, or chloro groups.

If not otherwise defined herein, the term "substituted" means optionally substituted at any position with varied C1-C4 alkyl, C1-C4 alkyloxy, fluoro, chloro, hydroxy, trifluoromethyl, trifluoromethoxy, methylenedioxy, cyano, or methoxymethyl groups.

The present invention relates to a process for the preparation of diverse known and novel cannabinoids 1 and 2 from the precursors 3 or 6 or mixtures of 3 with 6 via the intermediates 4 as the racemic modifications, or as the specific enantiomers shown below or as the enantiomers of 1 or 2 including $\Delta^9$-tetrahydrocannabinol (7), tetrahydrocannabivarin (9), cannabidiol (11), cannabidivarin (12) and other naturally occurring tetracyclic and tricyclic cannabinoids and other synthetic tetracyclic and tricyclic analogues from simple inexpensive starting materials using a cascade sequence of allylic rearrangement, aromatization and, for the tetracyclic cannabinoids 2, highly stereoselective and regioselective further cyclization producing the $\Delta^9$-cannabinoids 2 largely free from the undesired $\Delta^8$-isomers.

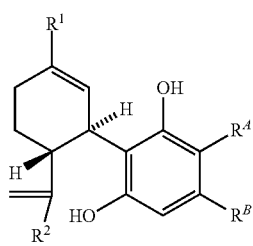

1

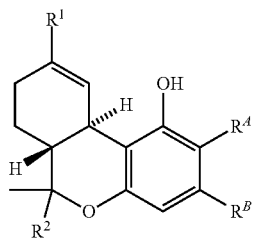

2

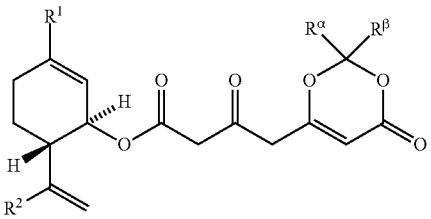

3

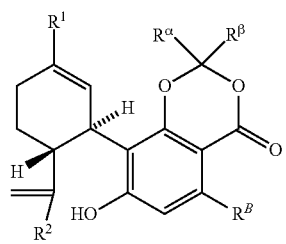

4

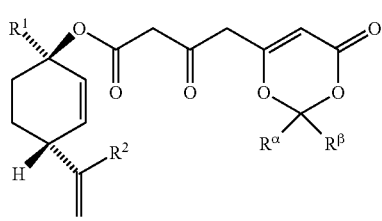

6 wherein:
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6;
$R\alpha$ and $R\beta$ are independently $C_1$ to $C_6$ alkyl or optionally substituted aryl or $R\alpha$ and $R\beta$ in combination are $(CH_2)_s$ (s is 4, 5 or 6) with $R\alpha$ and $R\beta$ being preferably both methyl.

The present invention also relates to a related process for the preparation of an intermediate of the formula 3 from reaction of the monoterpene starting materials 13 with the 1,3-dioxanediones 14 as the racemic modification or as mixtures of the two enantiomers in non-equal proportions, or as the specific enantiomer shown below or as the enantiomer of 3:

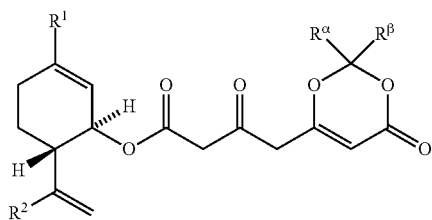

3

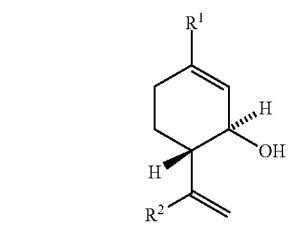

13

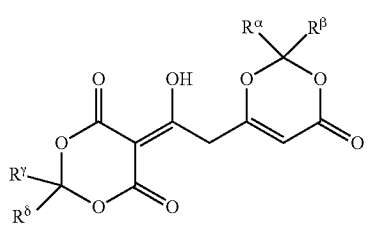

14 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

Rα and Rβ are independently $C_1$ to $C_6$ alkyl or optionally substituted aryl or Rα and Rβ in combination are $(CH_2)_s$;

Rγ is H, $C_1$ to $C_6$ alkyl and Rδ is optionally substituted aryl;

s is 4, 5 or 6.

The present invention also relates to a related process for the preparation of an intermediate of the formula 6 from reaction of the monoterpene starting materials 15 with the 1,3-dioxanediones 14 as the racemic modification or as mixtures of the two enantiomers in non-equal proportions, or as the specific enantiomer shown below or as the enantiomer of 6:

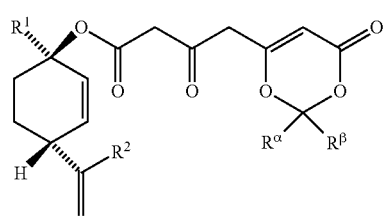

6

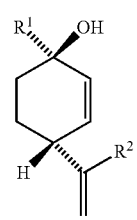

15

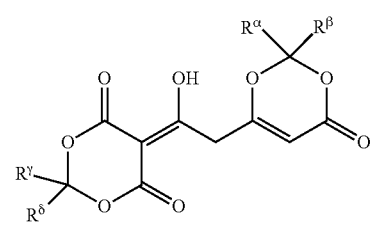

14 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

Rα and Rβ are independently $C_1$ to $C_6$ alkyl or optionally substituted aryl or Rα and Rβ in combination are $(CH_2)_s$;

Rγ is H, $C_1$ to $C_6$ alkyl and Rδ is optionally substituted aryl;

s is 4, 5 or 6.

The synthetic methods are suitable for use on a large scale and for manufacturing purposes. Examples of known cannabinoids that are available using the synthetic routes are cannabidiol (11), cannabidivarin (12), $\Delta^9$-tetrahydrocannabinol (7), tetrahydrocannabivarin (9) and compounds related to Nabilone (16).

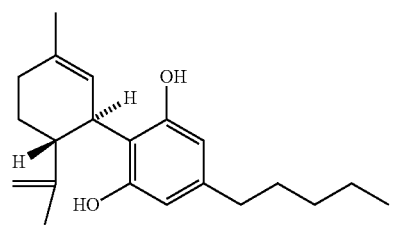

Cannabidiol (11)

-continued

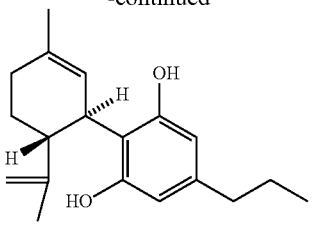
Cannabidivarin (12)

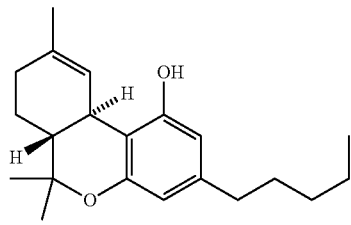
Tetrahydrocannabinol (7)

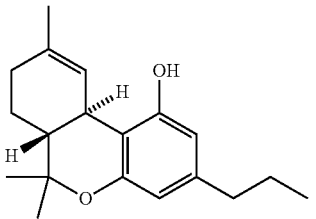
Tetrahydrocannabivarin (9)

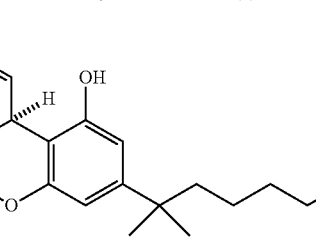
Nabilone (16)

The synthetic methods are also suitable for the synthesis of novel cannabinoids and these compounds are also part of the invention. The cannabinoids 1 below, which are novel analogs of cannabidiol (11) and cannabidivarin (12), are also available by the synthetic routes herein described and are part of the invention. These cannabinoids 1 have the formula:

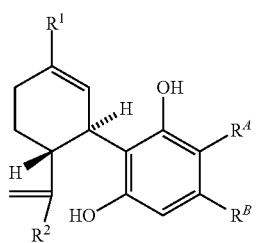

wherein:

$R^1$ is $C_2$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is H, $CO_2H$ and its pharmaceutically acceptable salts, $CO_2R^C$, $CONHR^D$, $CONR^DR^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6.

The aforementioned novel cannabinoids with the limited formulae 1 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 1 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administered to a patient by enteral, sublingual, intranasal, inhalation, rectal or parenteral drug administration or by other known methods of clinical administration.

The cannabinoids 1 below, which are also novel analogs of cannabidiol (11), cannabidivarin (12), are also available by the synthetic routes herein described and are part of the invention. These cannabinoids 1 have the formula:

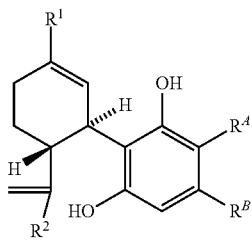

wherein:
R$^1$ is H, C$_1$ to C$_6$ alkyl, (CH$_2$)$_n$—C$_3$ to C$_6$ cycloalkyl, (CH$_2$)$_m$—OR$^3$;
R$^2$ is C$_2$ to C$_6$ alkyl, (CH$_2$)$_n$—C$_3$ to C$_6$ cycloalkyl, (CH$_2$)$_m$—OR$^3$;
n are independently 0, 1 or 2;
m are independently 1 or 2;
R$^3$ is H, CH$_3$, CH$_2$CH$_3$, CH$_2$CH$_2$CH$_3$ or CH(CH$_3$)$_2$;
R$^A$ is H, CO$_2$H and its pharmaceutically acceptable salts, CO$_2$R$^C$, CONHR$^D$, CONR$^D$R$^E$;
R$^B$ is H or C$_1$ to C$_2$ alkyl, linear or branched C$_3$ to C$_{10}$ alkyl or double branched C$_4$ to C$_{10}$ alkyl in each case optionally substituted by one or two hydroxyl groups or optionally substituted by one or more fluoro-groups, (CH$_2$)$_o$—C$_3$ to C$_6$ cycloalkyl, (CH$_2$)$_p$—OR$^F$, or C$_3$ to C$_6$ cycloalkyl optionally substituted by a C$_1$ to C$_8$ alkyl;
o is 0, 1, 2, 3, 4, 5 or 6;
p is 1, 2, 3, 4, 5 or 6;
R$^C$ is C$_1$ to C$_6$ alkyl, (CH$_2$)$_q$—C$_3$ to C$_6$ cycloalkyl, allyl, benzyl, substituted benzyl or 2-phenylethyl;
q is 0, 1, 2, 3, 4, 5 or 6;
R$^D$ is C$_1$ to C$_6$ alkyl, (CH$_2$)$_r$—C$_3$ to C$_6$ cycloalkyl, allyl, benzyl, substituted benzyl or 2-phenylethyl; R$^E$ is C$_1$ to C$_6$ alkyl, (CH$_2$)$_r$—C$_3$ to C$_6$ cycloalkyl, allyl, benzyl, substituted benzyl or 2-phenylethyl; or NR$^D$R$^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
R$^F$ is C$_1$ to C$_6$ alkyl, (CH$_2$)$_r$—C$_3$ to C$_6$ cycloalkyl;
r are independently 0, 1, 2, 3, 4, 5 or 6.

The aforementioned novel cannabinoids with the limited formulae 1 above may be used as active compounds either alone or admixed in combination with known cannabinoids such as but not limited to Δ$^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 1 above either alone or admixed in combination with known cannabinoids such as but not limited to Δ$^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administrated to a patient by enteral, sublingual, intranasal, inhalation, rectal or parenteral drug administration or by other known methods of clinical administration.

The cannabinoids 1 below, which are novel analogs of cannabidiol (11), cannabidivarin (12), are also available by the synthetic routes herein described and are part of the invention. These cannabinoids 1 have the formula:

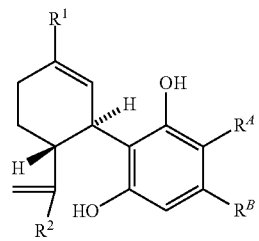

wherein:
R$^1$ is H, C$_1$ to C$_6$ alkyl, (CH$_2$)$_n$—C$_3$ to C$_6$ cycloalkyl, (CH$_2$)$_m$—OR$^3$;
R$^2$ is H, C$_1$ to C$_6$ alkyl, (CH$_2$)$_n$—C$_3$ to C$_6$ cycloalkyl, (CH$_2$)$_m$—OR$^3$;
n are independently 0, 1 or 2;
m are independently 1 or 2;
R$^3$ is H, CH$_3$, CH$_2$CH$_3$, CH$_2$CH$_2$CH$_3$ or CH(CH$_3$)$_2$;
R$^A$ is CONHR$^D$, CONR$^D$R$^E$;
R$^B$ is H or C$_1$ to C$_2$ alkyl, linear or branched C$_3$ to C$_{10}$ alkyl or double branched C$_4$ to C$_{10}$ alkyl in each case optionally substituted by one or two hydroxyl groups or optionally substituted by one or more fluoro-groups, (CH$_2$)$_o$—C$_3$ to C$_6$ cycloalkyl, (CH$_2$)$_p$—OR$^F$, or C$_3$ to C$_6$ cycloalkyl optionally substituted by a C$_1$ to C$_8$ alkyl;
o is 0, 1, 2, 3, 4, 5 or 6;
p is 1, 2, 3, 4, 5 or 6;
R$^C$ is C$_1$ to C$_6$ alkyl, (CH$_2$)$_q$—C$_3$ to C$_6$ cycloalkyl, allyl, benzyl, substituted benzyl or 2-phenylethyl;
q is 0, 1, 2, 3, 4, 5 or 6;
R$^D$ is C$_1$ to C$_6$ alkyl, (CH$_2$)$_r$—C$_3$ to C$_6$ cycloalkyl, C$_3$ to C$_6$ cycloalkyl, allyl, benzyl, substituted benzyl or 2-phenylethyl; R$^E$ is C$_1$ to C$_6$ alkyl, (CH$_2$)$_r$—C$_3$ to C$_6$ cycloalkyl, C$_3$ to C$_6$ cycloalkyl, allyl, benzyl, substituted benzyl or 2-phenylethyl; or NR$^D$R$^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
R$^F$ is C$_1$ to C$_6$ alkyl, (CH$_2$)$_r$—C$_3$ to C$_6$ cycloalkyl;
r are independently 0, 1, 2, 3, 4, 5 or 6.

The aforementioned novel cannabinoids with the limited formulae 1 above may be used as active compounds either alone or admixed in combination with known cannabinoids such as but not limited to Δ$^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, eye injury or disease including glaucoma, dry eye and retinal degeneration, disorders of immune-inflammation, pain, side effects of chemotherapy, anxiety, lung injury or disease, liver injury or disease, kidney injury or disease, amongst other pathologies. In some embodiments, the said novel cannabinoids with the limited formulae 1 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administrated to a patient by enteral, sublingual, intranasal, inhalation, topical, rectal or parenteral drug administration or by other known methods of clinical administration.

The dioxinone derivatives 3 below, which are intermediates for the synthesis of cannabinoids, are also available by the synthetic routes herein described and are part of the invention. These dioxinone derivatives 3 have the formula:

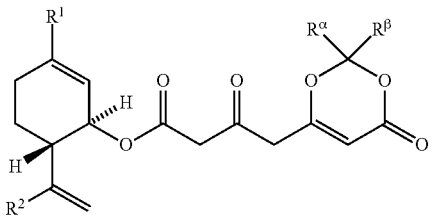

3 wherein
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is a hydroxyl protecting group, $CH_3$, $CH_2CH_3$, $CH_2CH_2CH_3$ or $CH(CH_3)_2$;
$R\alpha$ and $R\beta$ are independently $C_1$ to $C_6$ alkyl or optionally substituted aryl or $R\alpha$ and $R\beta$ in combination are $(CH_2)_s$;
s is 4, 5 or 6.

The dioxinone resorcylate derivatives 4 below, which are intermediates for the synthesis of cannabinoids, are also available by the synthetic routes herein described and are part of the invention. These dioxinone derivatives 4 have the formula:

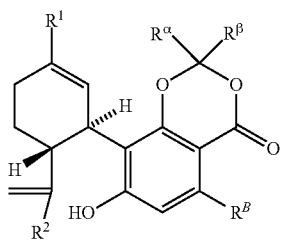

4 wherein:
$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^F$ is $C_1$ to $C_6$ alkyl, $(CH_2)_r$—$C_3$ to $C_6$ cycloalkyl;
r are independently is 0, 1, 2, 3, 4, 5 or 6;
$R\alpha$ and $R\beta$ are independently $C_1$ to $C_6$ alkyl or optionally substituted aryl or $R\alpha$ and $R\beta$ in combination are $(CH_2)_s$;
s is 4, 5 or 6.

The cannabinoids 2 below, which are novel analogs of $\Delta^9$-tetrahydrocannabinol (7) and tetrahydrocannabivarin (9), are also available by the synthetic routes herein described and are part of the invention. These cannabinoids 2 have the formula:

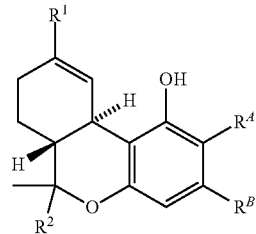

2 wherein
$R^1$ is $C_2$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^4$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6.

The aforementioned novel cannabinoids with the limited formulae 2 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's and neurodegenerative diseases, brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administrated to a patient by enteral, sublingual, intranasal, inhalation, rectal or parenteral drug, transdermal administration or by other known methods of clinical administration.

The cannabinoids 2 below, which are novel analogs of $\Delta^9$-tetrahydrocannabinol (7) and tetrahydrocannabivarin (9), are also available by the synthetic routes herein described and are part of the invention. These cannabinoids 2 have the formula:

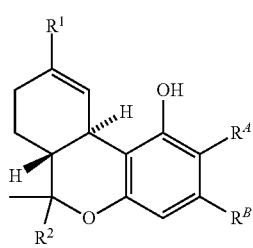

2 wherein $R^1$ is H, $C_1$ to $C_6$ alkyl, $(CH_2)_n$—$C_3$ to $C_6$ cycloalkyl, $(CH_2)_m$—$OR^3$;

$R^2$ is $C_2$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is H, $CO_2H$ and its pharmaceutically acceptable salts, $CO_2R^C$, $CONHR^D$, $CONR^DR^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6;

The aforementioned novel cannabinoids with the limited formulae 2 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administrated to a patient by enteral, sublingual, intranasal, inhalation, rectal or parenteral drug, transdermal administration or by other known methods of clinical administration.

The cannabinoids 2 below, which are also novel analogs of $\Delta^9$-tetrahydrocannabinol (7) and tetrahydrocannabivarin (9), are also available by the synthetic routes herein described and are part of the invention. These cannabinoids 2 have the formula:

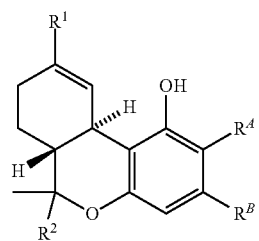

2 wherein $R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is $CONHR^D$, $CONR^DR^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, $C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl.

r are independently 0, 1, 2, 3, 4, 5 or 6.

The aforementioned novel cannabinoids with the limited formulae 2 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's and neurodegenerative diseases, brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients. The aforementioned pharmaceutical compositions may be administrated to a patient by enteral, sublingual, intranasal, inhalation, rectal or parenteral drug administration or by other known methods of clinical administration.

The dioxinone resorcylate derivatives 5 below, which are intermediates for the synthesis of cannabinoids, are also available by the synthetic routes herein described and are part of the invention. These dioxinone derivatives 5 have the formula:

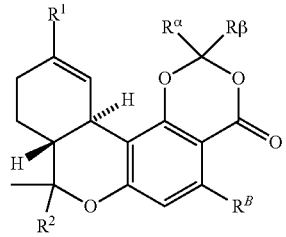

5 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^F$ is $C_1$ to $C_6$ alkyl, $(CH_2)_n$—$C_3$ to $C_6$ cycloalkyl;

Rα and Rβ are independently $C_1$ to $C_6$ alkyl or optionally substituted aryl or Rα and Rβ in combination are $(CH_2)_s$;

s is 4, 5 or 6.

The dioxinone derivatives 6 below, which are intermediates for the synthesis of cannabinoids, are also available by the synthetic routes herein described and are part of the invention. These dioxinone derivatives 6 have the formula:

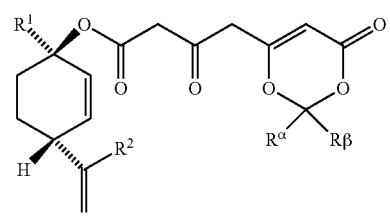

6 wherein $R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^F$ is $C_1$ to $C_6$ alkyl, $(CH_2)_n$—$C_3$ to $C_6$ cycloalkyl;

Rα and Rβ are independently $C_1$ to $C_6$ alkyl or optionally substituted aryl or Rα and Rβ in combination are $(CH_2)_s$;

s is 4, 5 or 6.

DETAILED DESCRIPTION OF THE INVENTION

Figure 1A:
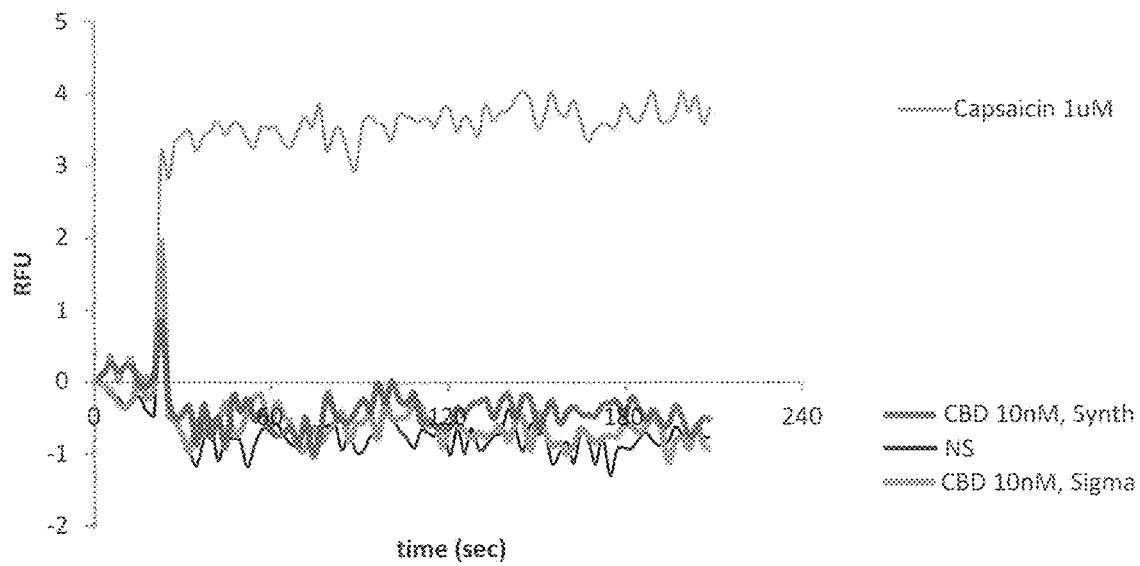
FIGS. 1A-1D show data for dose response and comparison in HEK-TRPV1 cells between Cannabidiol synthesized according to the disclosed embodiments to sourced "control" Cannabidiol.

The present invention relates to a process for the preparation of diverse known and novel cannabinoids 1 and 2 as the racemic modifications, or as the specific enantiomers shown below or as the enantiomers of 1 or 2 including $\Delta^9$-tetrahydrocannabinol (7), tetrahydrocannabivarin (9), cannabidiol (11), cannabidivarin (12) and other naturally occurring tetracyclic and tricyclic cannabinoids and other synthetic tetracyclic and tricyclic analogues from simple inexpensive starting materials using a cascade sequence of allylic rearrangement, aromatization and, for the tetracyclic cannabinoids 2, highly stereoselective and regioselective further cyclization producing the $\Delta^9$-cannabinoids 2 largely free from the undesired $\Delta^8$-isomers. The invention includes synthesis of the target cannabinoids as oils or crystalline derivatives, as appropriate, including solvates, hydrates and polymorphs.

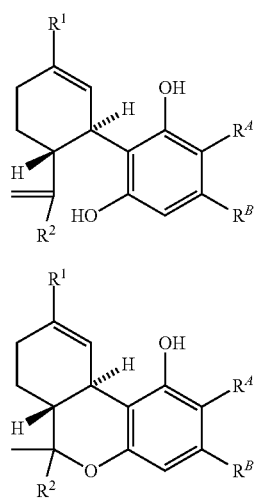

where:
R$^1$ is H, $C_1$ to $C_6$ alkyl, $(CH_2)_n$—$C_3$ to $C_6$ cycloalkyl, $(CH_2)_m$—OR$^3$;
R$^2$ is H, $C_1$ to $C_6$ alkyl, $(CH_2)_n$—$C_3$ to $C_6$ cycloalkyl, $(CH_2)_m$—OR$^3$;
n are independently 0, 1 or 2;
m are independently 1 or 2;
R$^3$ is H, $CH_3$, $CH_2CH_3$, $CH_2CH_2CH_3$ or $CH(CH_3)_2$;
R$^4$ is H, $CO_2H$ and its pharmaceutically acceptable salts, $CO_2R^C$, $CONHR^D$, $CONR^D R^E$;
R$^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—OR$^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
R$^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
R$^D$ is $C_1$ to $C_6$ alkyl, $(CH_2)_r$—$C_3$ to $C_6$ cycloalkyl, allyl, benzyl, substituted benzyl or 2-phenylethyl; R$^E$ is $C_1$ to $C_6$ alkyl, $(CH_2)_r$—$C_3$ to $C_6$ cycloalkyl, allyl, benzyl, substituted benzyl or 2-phenylethyl; or NR$^D$R$^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
R$^F$ is $C_1$ to $C_6$ alkyl, $(CH_2)_r$—$C_3$ to $C_6$ cycloalkyl;
r are independently 0, 1, 2, 3, 4, 5 or 6;
said process comprising:
treating a first intermediate of the formula 3 in which any hydroxyl group in R$^1$ and/or R$^2$ [wherein R$^2$ is $(CH_2)_m$—OH] is protected sequentially with (1) an acylating reagent R$^B$COY in which any hydroxyl group or groups in R$^B$ are protected in the presence of a first mild base 17 and also in the presence of a mild Lewis acid 18, (2) a palladium catalyst 19 with optional additional ligands 20 and (3) silica or an alternative equivalent solid reagent or a second mild base 21 followed by a Brønsted or Lewis acid 22 or a mild base alone such as cesium acetate and optional deprotection to provide the second intermediate 4 and secondly hydrolysis of said 4 with optional decarboxylation or by transesterification or by amide formation with optional deprotection as appropriate to provide 1;
wherein:
Y is a halogen preferably chlorine or R$^B$COY is an alternative reactive electrophilic acylating agent;
Rα and Rβ are independently $C_1$ to $C_6$ alkyl or optionally substituted aryl or Rα and Rβ in combination are $(CH_2)_s$ (s is 4, 5 or 6) with Rα and Rβ being preferably both methyl;
the first mild base 17 is an amine or a heterocyclic amine such as pyridine;
the mild Lewis acid 18 is preferably magnesium chloride;
the palladium catalyst 19 is either derived from a palladium(II) precatalyst or its itself a palladium(0) catalyst and the optional additional ligands 20 include but are not limited to one or more phosphines or diphosphines or their equivalents, preferably the palladium catalyst 19 and ligands 20 are specifically but not limited to phosphine complexes of palladium(0) such as tetrakis (triphenylphosphine)palladium(0) or tris(dibenzylideneacetone)dipalladium(0) [Pd$_2$(dba)$_3$] in the presence of a triarylphosphine or triheteroarylphosphine particularly tri-2-furylphosphine;
the second mild base 21 is cesium acetate or cesium carbonate or potassium carbonate;
the Brønsted or Lewis acid 22, if used, is acetic acid or hydrogen chloride.
wherein:
the optional hydroxyl-protecting group or groups are silyl protecting groups;

the optional hydroxyl-protecting group or groups are preferably independently t-butyldimethylsilyl, thexyldimethylsilyl, t-butyldiphenylsilyl or tri-iso-propylsilyl protecting groups.

Protecting groups are well known to persons skilled in the art and are described in textbooks such as Greene and Wuts, (P. G. M. Wuts, T. W. Greene, "Greene's Protective Groups in Organic Synthesis", 2006, Fourth Edition, John Wiley, New York).

Amide formation is carried out by activation of the carboxylic acid for example by formation of the N-hydroxysuccinimide ester and coupling with the corresponding amine, for example see Goto (Y. Goto, Y. Shima, S. Morimoto, Y. Shoyama, H. Murakami, A. Kusai and K. Nojima, "Determination of tetrahydrocannabinolic acid—carrier protein conjugate by matrix-assisted laser desorption/ionization mass spectrometry and antibody formation", *Organic Mass Spectrometry*, 1994, volume 29, pages 668-671). Alternative amide coupling reagents include but are not limited to dicyclohexyl carbodiimide (DCC), di-iso-propyl carbodiimide (DIC), O-(7-azabenzotriazol-1-yl)-1,1,3,3-tetramethyluronium hexafluorophosphate (HATU), O-(benzotriazol-1-yl)-1,1,3,3-tetramethyluronium hexafluorophosphate (HBTU) and bromotri(pyrrolidino)phosphonium hexafluorophosphate (PyBrop) (E. Valeur and M. Bradley, "Amide bond formation: beyond the myth of coupling reagents", Chemical Society Reviews, 2009, volume 38, pages 606-631).

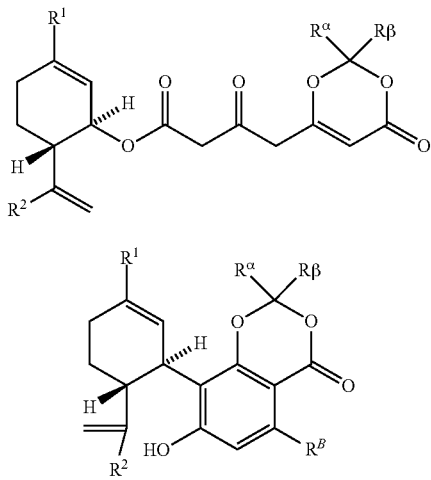

The present invention also relates to a related process for the preparation of diverse known and novel cannabinoids 1 and 2 as the racemic modifications, or as the specific enantiomers shown below or as the enantiomers of 1 or 2 including $\Delta^9$-tetrahydrocannabinol (7), tetrahydrocannabivarin (9), cannabidiol (11), cannabidivarin (12) and other naturally occurring tetracyclic and tricyclic cannabinoids and other synthetic tetracyclic and tricyclic analogues from simple inexpensive starting materials using a cascade sequence of allylic rearrangement, aromatization and, for the tetracyclic cannabinoids, further cyclization. The invention includes synthesis of the target cannabinoids as oils or crystalline derivatives, as appropriate, including solvates, hydrates and polymorphs.

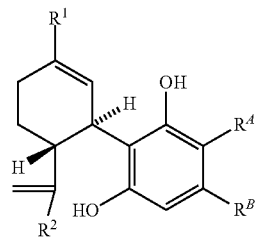

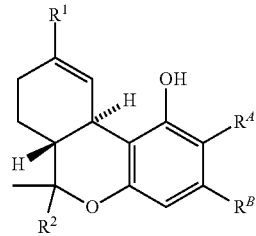

where:
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6;
said process comprising:
treating a first intermediate of the formula 6 in which any hydroxyl group in $R^1$ and/or $R^2$ [wherein $R^2$ is $(CH_2)_m$—OH] is protected sequentially with (1) an acylating reagent $R^BCOY$ in which any hydroxyl group or groups in $R^B$ are protected in the presence of a first mild base 17 and also in the presence of a mild Lewis acid 18, (2) a palladium catalyst 19 with optional additional ligands 20 and (3) silica or an alternative equivalent solid reagent or a second mild base 21 followed by a Brønsted or Lewis acid 22 or a mild base alone such as cesium acetate and optional deprotection to provide the second intermediate 4 and secondly hydrolysis of said 4 with optional decarboxylation or by transesterification or by amide formation with optional deprotection as appropriate to provide 1;
wherein:
Y is halogen preferably chlorine or $R^BCOY$ is an alternative reactive electrophilic acylating agent;
$R\alpha$ and $R\beta$ are independently $C_1$ to $C_6$ alkyl or optionally substituted aryl or $R\alpha$ and $R\beta$ in combination are $(CH_2)_s$ (s is 4, 5 or 6) with $R\alpha$ and $R\beta$ being preferably both methyl;
the first mild base 17 is an amine or a heterocyclic amine such as pyridine;
the mild Lewis acid 18 is preferably magnesium chloride;
the palladium catalyst 19 is either derived from a palladium(II) precatalyst or its itself a palladium(0) catalyst and the optional additional ligands 20 include but are not limited to one or more phosphines or diphosphines or their equivalents, preferably the palladium catalyst 19 and ligands 20 are specifically but not limited to phosphine complexes of palladium(0) such as tetrakis(triphenylphosphine)palladium(0) or tris(dibenzylideneacetone)dipalladium(0) [$Pd_2(dba)_3$] in the presence of a triarylphosphine or triheteroarylphosphine particularly tri-2-furylphosphine;
the second mild base 21 is cesium acetate or cesium carbonate or potassium carbonate;
the Brønsted or Lewis acid 22, if used, is acetic acid or hydrogen chloride.
wherein:
the optional hydroxyl-protecting group or groups are silyl protecting groups;
the optional hydroxyl-protecting group or groups are preferably independently t-butyldimethylsilyl, thexyldimethylsilyl, t-butyldiphenylsilyl or tri-iso-propylsilyl protecting groups.

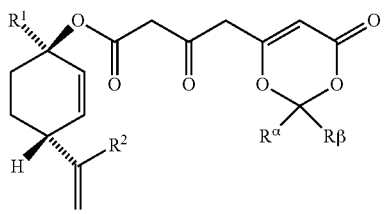

6

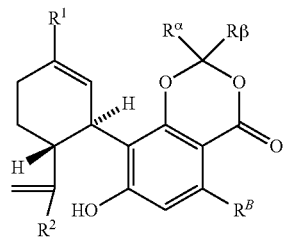

4

Protecting groups are well known to persons skilled in the art and are described in textbooks such as Greene and Wuts, (P. G. M. Wuts, T. W. Greene, "Greene's Protective Groups in Organic Synthesis", 2006, Fourth Edition, John Wiley, New York).

Of particular note in the invention is that the method of linking the terpene unit to the aromatic ring in intermediate 4 ensures, as a result of the π-allyl-palladium mediated step, the position of the alkene unit in the cyclohexene ring unit is formed regiospecifically as depicted in structure 4 and no other isomers are formed to any significant extent (for a discussion of the mechanism see R. Cookson, T. N. Barrett and A. G .M. Barrett, "β-Keto-dioxinones and β,δ-Diketo-dioxinones in Biomimetic Resorcylate Total Synthesis", Accounts of Chemical Research, 2015, volume 48, pages 628-642 and references therein).

Amide formation is carried out by activation of the carboxylic acid for example by formation of the N-hydroxysuccinimide ester and coupling with the corresponding amine, for example see Goto (Y. Goto, Y. Shima, S. Morimoto, Y. Shoyama, H. Murakami, A. Kusai and K. Nojima, "Determination of tetrahydrocannabinolic acid—carrier protein conjugate by matrix-assisted laser desorption/ionization mass spectrometry and antibody formation", Journal of Mass Spectrometry, 1994, volume 29, pages 668-671). Alternative amide coupling reagents include but are not limited to dicyclohexyl carbodiimide (DCC), di-isopropyl carbodiimide (DIC), O-(7-azabenzotriazol-1-yl)-1,1,3,3-tetramethyluronium hexafluorophosphate (HATU), O-(benzotriazol-1-yl)-1,1,3,3-tetramethyluronium hexafluorophosphate (H BTU) and bromotri(pyrrolidino)phosphonium hexafluorophosphate (PyBrop) (E. Valeur and M. Bradley, "Amide bond formation: beyond the myth of coupling reagents", Chemical Society Reviews, 2009, volume 38, pages 606-631).

The present invention also relates to a related process for the preparation of diverse known and novel cannabinoids 1 and 2 as the racemic modifications, or as the specific enantiomers shown below or as the enantiomers of 1 or 2 including $\Delta^9$-tetrahydrocannabinol (7), tetrahydrocannabivarin (9), cannabidiol (11), cannabidivarin (12) and other naturally occurring tetracyclic and tricyclic cannabinoids and other synthetic tetracyclic and tricyclic analogues from mixtures of the intermediates 3 and 6 simple inexpensive starting materials using a cascade sequence of allylic rearrangement, aromatization to produce the resorcylate derivatives 4 and, for the tetracyclic cannabinoids, further cyclization.

It should be noted that several of the intermediates in these syntheses can exist as keto-and enol tautomers. The depiction of a structure as a keto-form also includes the corresponding enol-form including mixtures containing both keto- and enol forms.

Additionally, the depiction of a structure as an enol-form also includes the corresponding keto-form including mixtures containing both keto- and enol forms. By way of examples, intermediates 3 and 6 exist as mixtures of both keto- and enol forms although the structures, for reasons of simplicity, are drawn as the keto-forms. Additionally, it should be noted that whilst a structure is drawn as a particular stereoisomer and enantiomer, the invention also includes the enantiomeric compounds, racemic compounds and mixtures of the two enantiomers in non-equal proportions. Additionally, the invention also covers structurally feasible diastereoisomers. The invention includes synthesis of the target cannabinoids as oils or crystalline derivatives, as appropriate, including solvates, hydrates and polymorphs.

The present invention also relates to a related process for the preparation of diverse cannabinoids of the formula 2 as the racemic modification or as mixtures of the two enantiomers in non-equal proportions, or as the specific enantiomer shown below or as the enantiomer of 2:

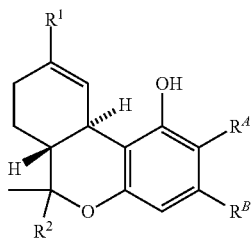

2

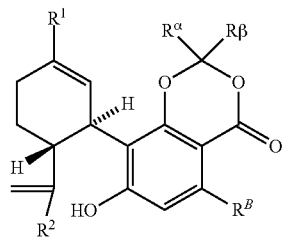

4

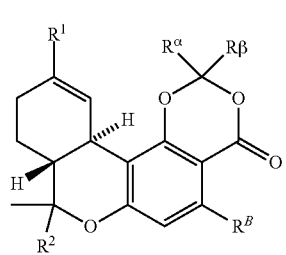

5 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is H, $CO_2H$ and its pharmaceutically acceptable salts, $CO_2R^C$, $CONHR^D$, $CONR^D R^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^D R^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6;

Rα and Rβ are independently $C_1$ to $C_6$ alkyl or optionally substituted aryl or Rα and Rβ in combination are $(CH_2)_s$;

s is 4, 5 or 6;

said process comprising:

treating a first intermediate of the formula 4 or the cannabinoid 1 in which any hydroxyl group or groups in $R^1$, $R^2$ [wherein $R^2$ is $(CH_2)_m$—OH] and/or $R^B$ are protected with (1) a Lewis acid 23 and secondly treating the resultant intermediate 5 by hydrolysis with optional decarboxylation or by transesterification or by amide formation with optional deprotection as appropriate to provide 2;

wherein:

Rα and Rβ are both preferably methyl;

the Lewis acid 23 is a derivative of a metal or metalloid such as but not limited to boron(III), aluminum(III), zinc(II), tin(IV), titanium(IV), zirconium(IV), scandium(III), a lanthanide(III) or bismuth(III) or an inorganic solid such as a zeolite or an equivalent or is replaced by a Brønsted acid such as but not limited to methanesulfonic acid, 4-toluenesulfonic acid or hydrogen chloride or any combination of such a Lewis acid and Brønsted acid, Lewis acid and inorganic solid; Brønsted acid and inorganic solid or Lewis acid, Brønsted acid and inorganic solid;

the Lewis acid 23 is alternatively a derivative of boron (III) such as boron trifluoride or boron trifluoride etherate;

the Lewis acid 23 is alternatively a derivative of aluminum(III) such as aluminum chloride, ethylaluminum dichloride or diethylaluminum chloride;

the Lewis acid 23 is alternatively a derivative of zinc(II) such as zinc chloride or zinc bromide;

the Lewis acid 23 is alternatively a derivative of tin(IV) such as stannic chloride;

the Lewis acid 23 is alternatively a derivative of titanium (IV) such as titanium tetrachloride or iso-propoxytitanium trichloride;

the Lewis acid 23 is alternatively a derivative of zirconium(IV) such as zirconium tetrachloride;

the Lewis acid 23 is alternatively a derivative of scandium (III) such as scandium tris-trifluoromethanesulfonate or scandium tris-(di-(trifluoromethanesulfonyl)amide or scandium tris-(tri-(trifluoromethanesulfonyl)methide;

the Lewis acid 23 is alternatively a derivative of lanthanide(III) such as ytterbium tris-trifluoromethanesulfonate or ytterbium tris-(di-(trifluoromethanesulfonyl)amide or ytterbium tris-(tri-(trifluoromethanesulfonyl)methide;

the Lewis acid 23 is alternatively a derivative of bismuth (III) such as bismuth tris-trifluoromethanesulfonate or bismuth tris-(di-(trifluoromethanesulfonyl)amide or bismuth tris-(tri-(trifluoromethanesulfonyl)methide.

wherein:

the hydroxyl protecting group or groups are silyl protecting groups;

the hydroxyl protecting group or groups are preferably independently t-butyldimethylsilyl, thexyldimethylsilyl, t-butyldiphenylsilyl or tri-iso-propylsilyl protecting groups.

Protecting groups are well known to persons skilled in the art and are described in textbooks such as Greene and Wuts, (P. G. M. Wuts, T. W. Greene, "Greene's Protective Groups in Organic Synthesis", 2006, Fourth Edition, John Wiley, New York).

Amide formation is carried out by activation of the carboxylic acid for example by formation of the N-hydroxysuccinimide ester and coupling with the corresponding amine, for example see Goto (Y. Goto, Y. Shima, S. Morimoto, Y. Shoyama, H. Murakami, A. Kusai and K. Nojima, "Determination of tetrahydrocannabinolic acid—carrier protein conjugate by matrix-assisted laser desorption/ionization mass spectrometry and antibody formation", Journal of Mass Spectrometry, 1994, volume 29, pages 668-671). Alternative amide coupling reagents include but are not limited to dicyclohexyl carbodiimide (DCC), di-iso-propyl carbodiimide (DIC), O-(7-azabenzotriazol-1-yl)-1,1,3,3-tetramethyluronium hexafluorophosphate (HATU), O-(benzotriazol-1-yl)-1,1,3,3-tetramethyluronium hexafluorophosphate (HBTU) and bromotri(pyrrolidino)phosphonium hexafluorophosphate (PyBrop) (E. Valeur and M. Bradley, "Amide bond formation: beyond the myth of coupling reagents", Chemical Society Reviews, 2009, volume 38, pages 606-631).

The Lewis acid 23 mediated cyclization reactions of cannabinoids 4 to cannabinoids 5 is known for related compounds that lack this key RαRβC ketal unit such as in examples of the cannabinoids 1 and the extension of this reaction to compounds with this unit is part of the invention. Such indirect precedent includes publications by Rhee, Childers, Gaoni, Adams, Glaser, Koch, Steup, Burdick, Kupper and Gutman (M.-H. Rhee, Z. Vogel, J. Barg, M. Bayewitch, R. Levy, L. Hanus, A. Breuer and R. Mechoulam, "Cannabinol Derivatives: Binding to Cannabinoid Receptors and Inhibition of Adenylylcyclase", *Journal of Medicinal Chemistry*, 1997, volume 40, pages 3228-3233; W. E. Childers, Jr., H. W. Pinnick, "A Novel Approach to the Synthesis of the Cannabinoids", *Journal of Organic Chemistry*, 1984, volume 49, pages 5276-5277; Y. Gaoni and R. Mechoulam "Isolation, Structure, and Partial Synthesis of an Active Constituent of Hashish", *The Journal of the American Chemical Society*, 1964, volume 86, pages 1646-1647; R. Adams, D. C. Pease, C. K. Cain and J. H. Clark, "Structure of Cannabidiol. VI. Isomerization of Cannabidiol to Tetrahydrocannabinol, a Physiologically Active Product. Conversion of Cannabidiol to Cannabinol", *The Journal of the American Chemical Society*, 1940, volume 62, pages 2402-2405; R. Glaser, I. Adin, R. Machoulam and L. Hanus, "2-Methyl- and 4-Methyl-Δ⁸-tetrahydrocannabinol: Correlation of Spatial Distinction with Cannabinoid Receptor Binding", *Heterocycles*, 1994, volume 39, pages 867-877; O. Koch, M. R. Götz, J. Looft and T. Vössing, "Mixtures of cannabinoid compounds, and production and use thereof", US Patent Application 2015/0336874 Al; C. Steup and T. Herkenroth, "Process for preparing synthetic cannabinoids", US Patent Application 2010/298579 Al; D. C. Burdick, S. J. Collier, F. Jos, B. Biolatto, B. J. Paul, H. Meckler, M. A. Helle, A. J. Habershaw, "Process for production of delta-9-tetrahydrocannabinol", U.S. Pat. No. 7,674,922 B2 (2010); R. J. Kupper, "Cannabinoid active pharmaceutical ingredient for improved dosage forms", WO2006/133941 A2; Erler and S. Heitner, "Method for the production of Dronabinol from Cannabidiol, using a molecular sieve", WO2006/136273 Al; A. L. Gutman, M. Etinger, I. Fedotev, R. Khanolkar, G. A. Nisnevich, B. Pertsikov, I. Rukhman and B. Tishin, "Methods for purifying trans-H-(−)-Δ⁹-tetrahydrocannabinol and trans-(+)-Δ⁹-tetrahydrocannabinol", U.S. Pat. No. 9,278,083 B2). In consequence, hydrolysis with optional decarboxylation or by transesterification or by amide formation with optional deprotection as appropriate provides the Δ⁹-cannabinoids 2 with very low levels of the undesired Δ⁸-cannabinoids. The use of the RαRβC ketal unit to control the regioselectivity of reaction is inventive, however the mono-protection of cannabidiol as a methyl ether, generated in situ, was reported to be regiospecific for the synthesis of Δ⁹-tetrahydrocannabinol (7) (W. E. Childers, Jr. and H. W. Pinnick, "A Novel Approach to the Synthesis of the Cannabinoids", The Journal of Organic Chemistry, 1984, volume 49, pages 5276-5277).

The present invention also relates to a related process for the preparation of an intermediate of the formula 3 as the racemic modification or as mixtures of the two enantiomers in non-equal proportions, or as the specific enantiomer shown below or as the enantiomer of 3:

3

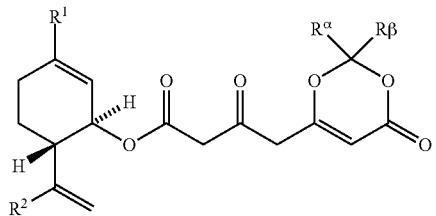

wherein:
R¹ is H, $C_1$ to $C_6$ alkyl, $(CH_2)_n$—$C_3$ to $C_6$ cycloalkyl, $(CH_2)_m$—$OR^3$;
R² is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
R³ is H, $CH_3$, $CH_2CH_3$, $CH_2CH_2CH_3$ or $CH(CH_3)_2$;
Rα and Rβ are independently $C_1$ to $C_6$ alkyl or optionally substituted aryl or Rα and Rβ in combination are $(CH_2)_s$;
s is 4, 5 or 6;
said process comprising:
treating intermediate of the formula 13 in which any hydroxyl group in R¹ and/or R² [wherein R² is $(CH_2)_m$—OH] is protected with the mild acylating agent 14 in an inert solvent at a temperature of 40 to 100° C. to produce intermediate 3 retaining as appropriate said hydroxyl protecting group.

13

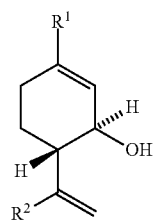

-continued

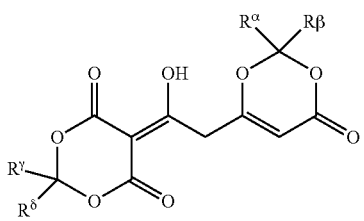

14 wherein:
the inert solvent is a halogenated solvent or an aromatic hydrocarbon;
the inert solvent is preferably an aromatic hydrocarbon such as toluene;
the temperature of reaction is preferably 40 to 60° C.;
preferably the temperature of reaction is 50° C. and the solvent is toluene.
wherein:
the hydroxyl-protecting group or groups are silyl protecting groups;
the hydroxyl-protecting group or groups are preferably independently t-butyldimethylsilyl, thexyldimethylsilyl, t-butyldiphenylsilyl or tri-iso-propylsilyl protecting groups.

Protecting groups are well known to persons skilled in the art and are described in textbooks such as Greene and Wuts, (P. G. M. Wuts, T. W. Greene, "Greene's Protective Groups in Organic Synthesis", 2006, Fourth Edition, John Wiley, New York).

The present invention also relates to a related process for the preparation of an intermediate of the formula 6 as the racemic modification or as mixtures of the two enantiomers in non-equal proportions, or as the specific enantiomer shown below or as the enantiomer of 6:

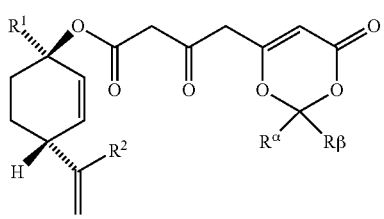

6 wherein:
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R\alpha$ and $R\beta$ are independently $C_1$ to $C_6$ alkyl or optionally substituted aryl or $R\alpha$ and $R\beta$ in combination are $(CH_2)_s$;
s is 4, 5 or 6;
said process comprising:
treating intermediate of the formula 15 in which any hydroxyl group in $R^1$ and/or $R^2$ [wherein $R^2$ is $(CH_2)_m$—OH] is protected with the mild acylating agent 14 in an inert solvent at a temperature of 40 to 100° C. to produce intermediate 6.

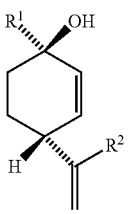

15

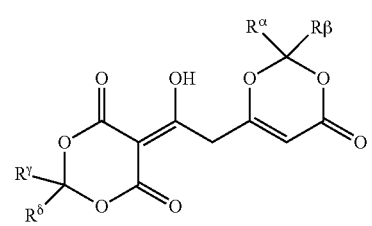

14 wherein:
the inert solvent is a halogenated solvent or an aromatic hydrocarbon;
the inert solvent is preferably an aromatic hydrocarbon such as toluene;
the temperature of reaction is preferably 40 to 60° C.;
preferably the temperature of reaction is 50° C. and the solvent is toluene.
wherein:
the hydroxyl-protecting group or groups are silyl protecting groups;
the hydroxyl-protecting group or groups are preferably independently t-butyldimethylsilyl, thexyldimethylsilyl, t-butyldiphenylsilyl or tri-iso-propylsilyl protecting groups.

Protecting groups are well known to persons skilled in the art and are described in textbooks such as Greene and Wuts, (P. G. M. Wuts, T. W. Greene, "Greene's Protective Groups in Organic Synthesis", 2006, Fourth Edition, John Wiley, New York).

An example of the new method is given in Scheme 1 below. The keto-ester dioxinone 24 is synthesized from the keto-dioxinone 29 and imidazolide 30 or an equivalent reagent such as, but not limited to a benzotriazole carbonate derivative or a 4-nitrophenyl carbonate, using methods equivalent to those published for other related keto-ester dioxinones (R. Cookson, T. N. Barrett and A. G. M. Barrett, "β-Keto-dioxinones and β,δ-Diketo-dioxinones in Biomimetic Resorcylate Total Synthesis", *Accounts of Chemical Research,* 2015, volume 48, pages 628-642 and references therein).

C-Acylation of keto-ester dioxinone 24 is carried out using hexanoyl chloride in the presence of a base such as pyridine in the presence of magnesium chloride to provide the corresponding adduct 25. This may be isolated and purified but, in a preferred embodiment, is taken directly to the next stage. Subsequent decarboxylation and allylic rearrangement using methods equivalent to those published for other related diketo-dioxinones (R. Cookson, T. N. Barrett and A. G. M. Barrett, "β-Keto-dioxinones and β,δ-Diketo-dioxinones in Biomimetic Resorcylate Total Synthesis", *Accounts of Chemical Research,* 2015, volume 48, pages 628-642 and references therein) provides the corresponding β,δ-diketo-dioxinone 26 with the monoterpene unit attached at the a-carbon. Typical catalysts for the conversion of intermediate 25 into diketo-dioxinone 26 include palladium (0) catalysts, which may be already at the palladium(0) oxidation state such as Pd(PPh$_3$)$_4$ or as a palladium(II) pre-catalyst in the presence of a phosphine or equivalent monodentate or alternative bidentate or higher dentate ligands. Alternative metal catalysts may be employed for the conversion of 25 into 26 including but not limited to complexes of iron or molybdenum, which are known to a person skilled in the art to be of use in metal-catalyzed reactions that proceed via π-allyl metal intermediates.

SCHEME 1

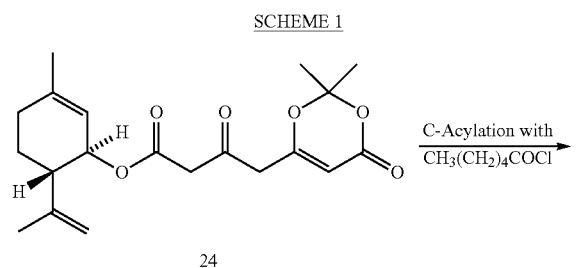

24

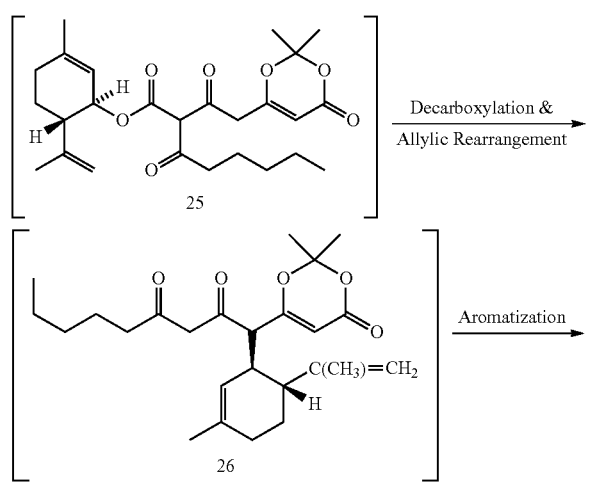

25

26

27

28

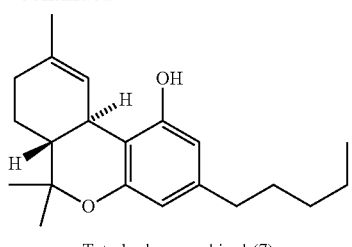

Tetrahydrocannabinol (7)

Intermediate 26 may be isolated and purified but, in a preferred embodiment, is taken directly to the next stage without isolation. Reaction of the diketo-dioxinone 26 with a second catalyst such as silica gel or cesium carbonate followed by hydrochloric acid produces the resorcylate derivative 27. Alternative catalysts for this aromatization reaction are given in the Accounts of Chemical Research paper cited above. In the most preferred embodiment of the reaction, the keto-ester 24 is converted in a single vessel via intermediates 25 and 26 into the resorcylate 27 without any isolation and purification except for the product 27, a derivative of cannabidiol (11).

Cyclization of 27 using boron trifluoride etherate as reported in the synthesis of hongoquercin B (T. N. Barrett and A. G. M. Barrett, "Cascade Polyketide and Polyene Cyclizations: Biomimetic Total Synthesis of Hongoquercin B", *The Journal of the American Chemical Society*, 2014, volume 136, pages 17013-17015) or with other Lewis or Brønsted acids or Lewis/Brønsted acid combinations well known to a person skilled in the art in the cannabinoid area provides the Δ$^1$-tetrahydrocannabinolic acid derivative 28.

Cleavage of the dioxinone rings of intermediate 28 by saponification or an equivalent process as described in the Accounts of Chemical Research paper cited above gives Δ$^1$-tetrahydrocannabinolic acid (31). Decarboxylation of Δ$^1$-tetrahydrocannabinolic acid (31) provides tetrahydrocannabinol (7) (see H. Perrotin-Brunel, W. Buijs, J. van Spronsen, M. J. E. van Roosmalen, C. J. Peters, R. Verpoorte and G.-J. Witkamp, "Decarboxylation of Δ$^9$-tetrahydrocannabinol: Kinetics and molecular modeling", Journal of Molecular Structure, 2011, volume 987, pages 67-73 and references therein). In the same way, saponification or an equivalent process and decarboxylation of intermediate 27 gives cannabidiol (11).

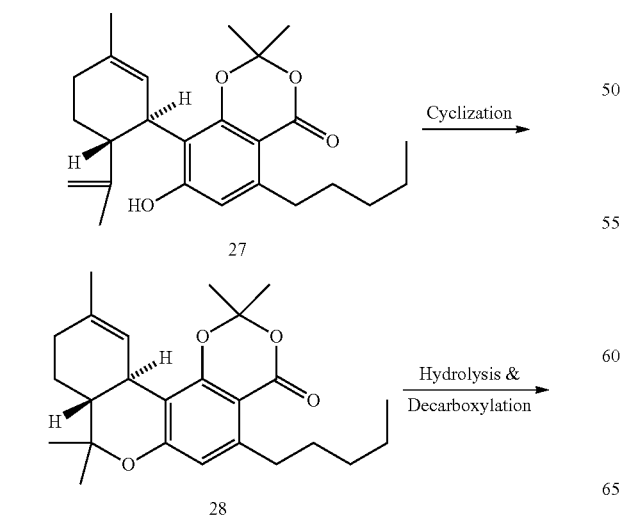

29

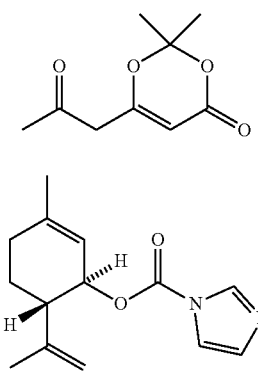

30

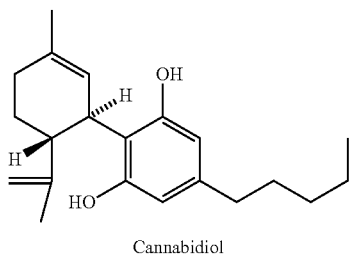

Cannabidiol (11)

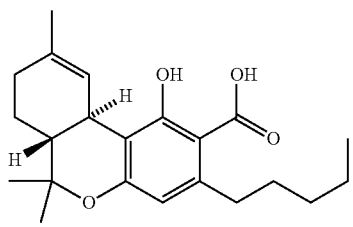

Δ¹-Tetrahydrocannabinolic Acid (31)

It additionally needs to be stressed that since the starting materials are pure, e.g. hexanoyl chloride contains no butanoyl chloride, the product cannabinoids with n-pentyl side chains, for example Δ⁹-tetrahydrocannabinol (7), are not contaminated by the corresponding cannabinoids with n-propyl side chains such as cannabidivarin (12) and tetrahydrocannabivarin (9). In addition, since the methods used for the link-up of the aromatic core to the terpene unit are so mild and regiospecific, the products are much easier to purify than those produced with classical synthetic routes, which may contain impurities derived from well-known monoterpene rearrangements as well as other contaminants.

It should be noted that the synthesis in Scheme 1 is carried out with equivalent starting materials. For example, the sequence is carried out starting with the terpene 32 with the protected 2-hydroxy-propyl group or alternative terpene compounds. In these cases, intermediates with the protected 2-hydroxy-propyl group corresponding to 30, 25, 26 and 27 as well as that corresponding to 11 also retain the same substituent.

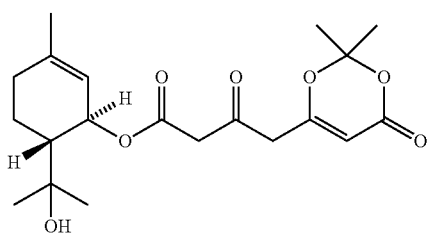

32

It should be noted that the synthesis in Scheme 1 is carried out replacing hexanoyl chloride with butanoyl chloride as in Scheme 2. The steps directly parallel those in the earlier scheme and provide tetrahydrocannabivarin (9) and cannabidivarin (12) and the C-3 analogue of Δ¹-tetrahydrocannabinolic acid (31) above and rely upon the equivalent inventive steps.

It needs also to be stressed that since the starting materials are pure, e.g. butanoyl chloride contains no hexanoyl chloride, the product cannabinoids with n-propyl side chains are not contaminated by the corresponding cannabinoids with n-pentyl side chains such as cannabidiol (11) and Δ⁹-tetrahydrocannabinol (7). In addition, since the methods used for the link-up of the aromatic core to the terpene unit are so mild and regiospecific, the products are much easier to purify than those produced with classical synthetic routes, which may contain impurities derived from well-known monoterpene rearrangements as well as other contaminants. It also needs to be stressed the invention is that the use of the $Me_2C$ ketal unit ensures that the cyclization reaction to produce the cannabinoid 36 provides only the Δ⁹-isomer and the undesired Δ⁸-isomer is not formed to any significant extent. In consequence, hydrolysis with decarboxylation provides tetrahydrocannabivarin (9) as the Δ⁹-isomer with very low levels of the undesired Δ⁸-isomer.

SCHEME 2

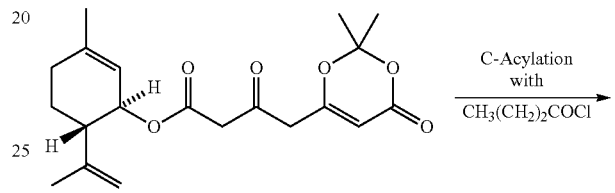

24

C-Acylation with $CH_3(CH_2)_2COCl$

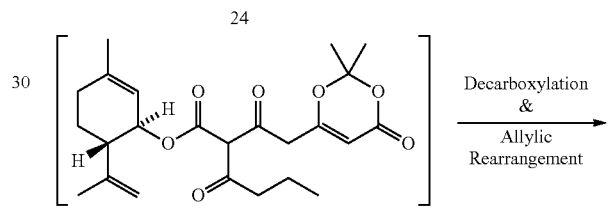

33

Decarboxylation & Allylic Rearrangement

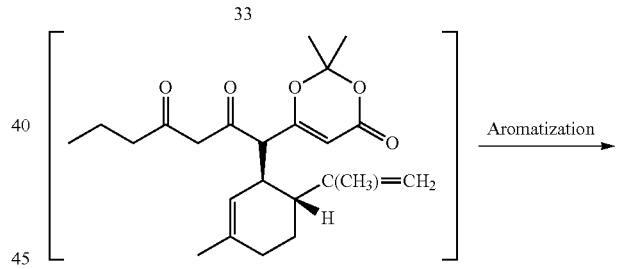

34

Aromatization

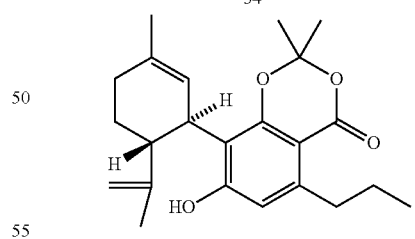

35

Cyclization

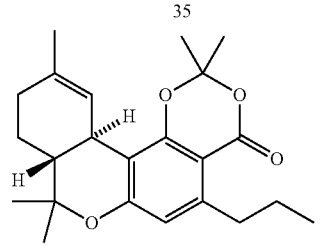

36

Hydrolysis & Decarboxylation

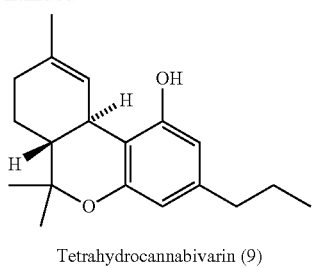

Tetrahydrocannabivarin (9)

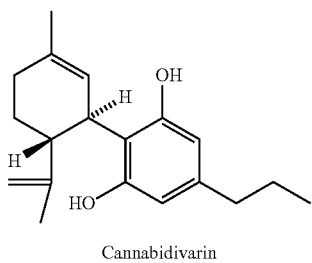

(12)

Cannabidivarin

The methods of Schemes 1 and 2 are also of use for the concise synthesis of families of cannabinoids with hitherto unknown ring substituents from the C-acylation of dioxinone 37 with the carboxylic acyl chlorides 38, decarboxylative allylic rearrangement, aromatization and hydrolysis and decarboxylation. Examples of such novel cannabinoids include but are not limited to the analogues 39 and 40 ($R^1$=a $C_2$ to $C_5$ alkyl, cyclopropyl, phenyl with $R^2$=n-pentyl) and ($R^1$=CHs with $R^2$=cyclopropyl, cyclobutyl, cyclopentyl, phenyl) as well as "inverted" analogues 39 and 40 ($R^1$=n-pentyl, $R^2$=CH$_3$). The invention includes synthesis of the target cannabinoids as oils or crystalline derivatives, as appropriate, including solvates, hydrates and polymorphs.

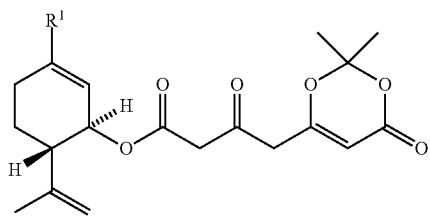

37

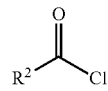

38

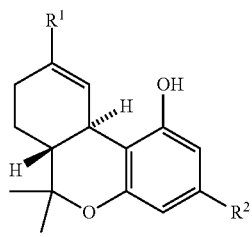

39

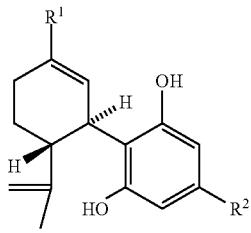

40

The aforementioned novel cannabinoids with formulae 39 and 40 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with formulae 39 and 40 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, flavors and fragrances such as but not limited to the volatile terpenes of Cannabis and citrus fruits and other pharmaceutically acceptable diluents or excipients. The aforementioned pharmaceutical compositions may be administrated to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

In another embodiment of the invention the key intermediates for the decarboxylation, allylic rearrangement and aromatization steps are prepared using the methods shown in Schemes 3 and 4. Terpene allylic alcohol building blocks such as 41 or 44 undergo reaction with dioxanedione 14 under mild heating to give the corresponding dioxinone β-keto-esters, 42 or 45 respectively. In a preferred embodiment reaction is carried out with alcohol 41 or alcohol 44 with reagent 14 (Rα=Rβ=Rγ=methyl, Rδ=phenyl or Rα=Rβ=methyl, Rγ=H, Rδ=phenyl) at a temperature of between 50° C. and 60° C. However, it should be noted that an alternative dioxanedione 14 may be used provided that the substituents Rα, Rβ, Rγ and Rδ are chosen such that addition of the terpene alcohol occurs at the dione moiety exclusively. For example, Rα and Rβ in combination can be $(CH_2)_n$ (n=4, 5) with Rγ and Rδ both as methyl.

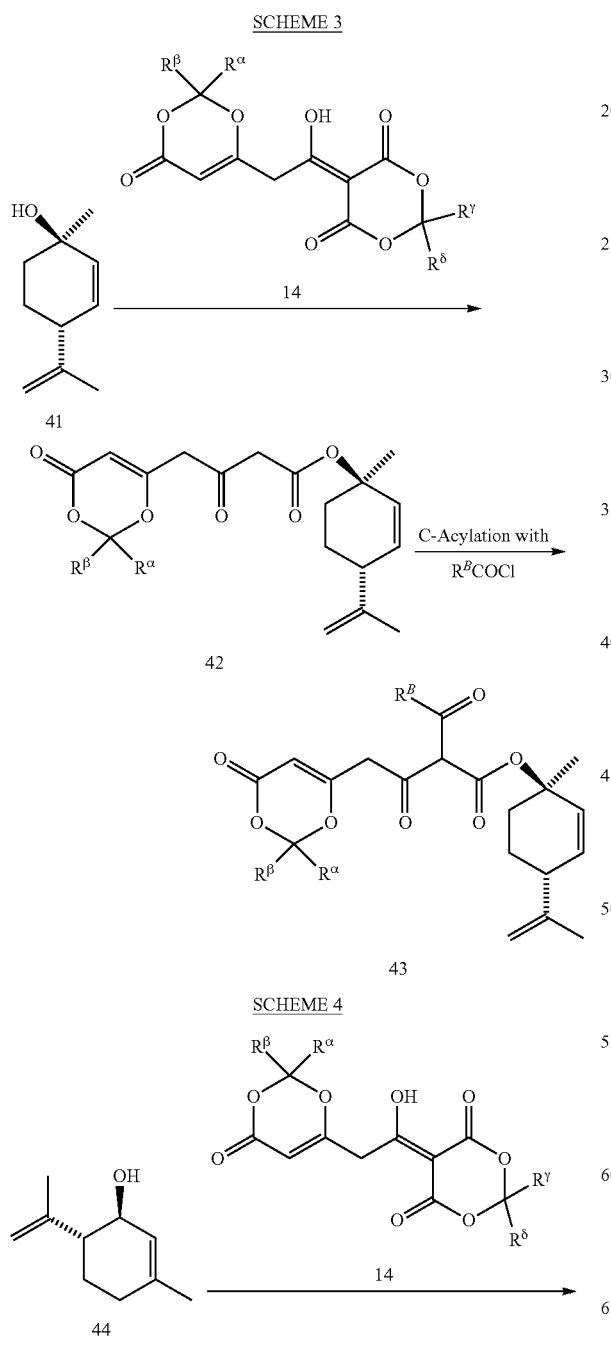

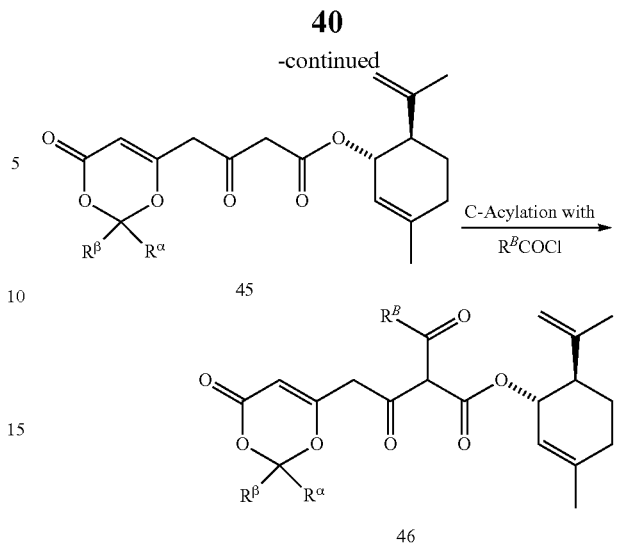

Dioxanedione 14 is prepared by coupling Meldrum's acid derivative 48 with carboxylic acid 47 and an appropriate activating agent such as (but not limited to) N,N'-dicyclohexyl carbodiimide (DCC) or an equivalent (see D. C. Elliott, T.-K. Ma, A. Selmani, R. Cookson, P. J. Parsons, and A. G. M. Barrett "Sequential Ketene Generation from Dioxane-4,6-dione-keto-dioxinones for the Synthesis of Terpenoid Resorcylates", Organic Letters, 2016, volume 18, pages 1800 to 1803).

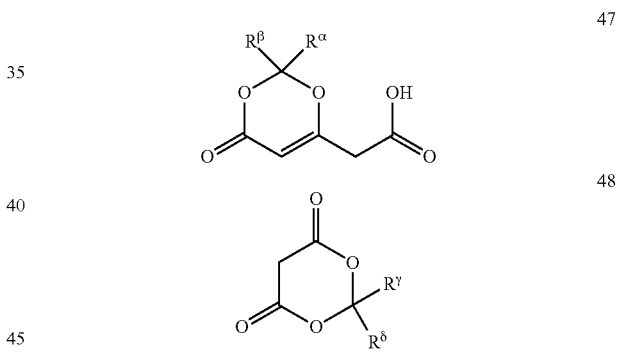

The C-acylation of compounds 42 or 45 are carried out with an appropriate acylating agent such as $R^BCOX$ where X=Cl, Br, $OSO_2CF_3$, etc. In a preferred embodiment hexanoyl chloride is used (X=Cl) and $R^B$=$(CH_2)_4CH_3$ in the presence of magnesium chloride and a base such as pyridine to give diketo-dioxinones 43 and 46 respectively. Preferably without further purification, the crude esters 43 and 46 either as separate compounds or as mixtures of these two regioisomers are subjected to the previously mentioned decarboxylation and allylic rearrangement via palladium catalysis to give the corresponding β,δ-diketo-dioxinones 49 with the monoterpene unit attached at specifically the γ-carbon as illustrated in Scheme 5. Typical catalysts for the conversion of intermediate 43 and 46 into diketo-dioxinone 49 include palladium(0) catalysts such as $Pd_2dba_3$ in the presence of a phosphine or equivalent monodentate ligand such as $P(2-furyl)_3$. Alternative catalysts may also be used by someone skilled in the art as previously discussed above.

Intermediate 49 is converted directly to the next stage intermediate preferably without isolation and purification.

Thus reaction of the diketo-dioxinone 49 with a second catalyst such as cesium acetate produces the resorcylate derivative 50. Conversion of the resorcylate derivative 50 into intermediate 51 and cannabinoids such as 52 and 53 are carried out by methods as previously discussed above.

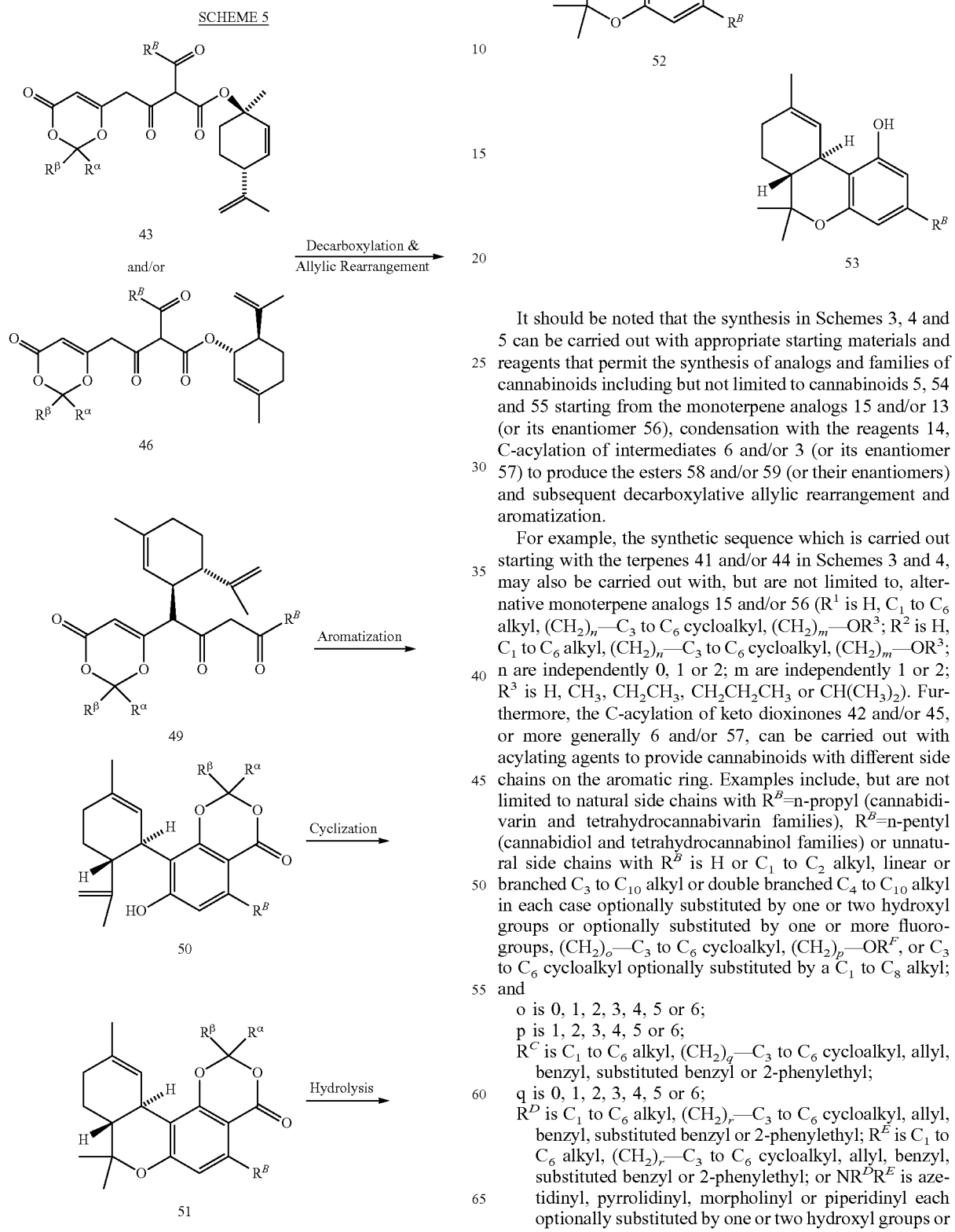

It should be noted that the synthesis in Schemes 3, 4 and 5 can be carried out with appropriate starting materials and reagents that permit the synthesis of analogs and families of cannabinoids including but not limited to cannabinoids 5, 54 and 55 starting from the monoterpene analogs 15 and/or 13 (or its enantiomer 56), condensation with the reagents 14, C-acylation of intermediates 6 and/or 3 (or its enantiomer 57) to produce the esters 58 and/or 59 (or their enantiomers) and subsequent decarboxylative allylic rearrangement and aromatization.

For example, the synthetic sequence which is carried out starting with the terpenes 41 and/or 44 in Schemes 3 and 4, may also be carried out with, but are not limited to, alternative monoterpene analogs 15 and/or 56 ($R^1$ is H, $C_1$ to $C_6$ alkyl, $(CH_2)_n$—$C_3$ to $C_6$ cycloalkyl, $(CH_2)_m$—$OR^3$; $R^2$ is H, $C_1$ to $C_6$ alkyl, $(CH_2)_n$—$C_3$ to $C_6$ cycloalkyl, $(CH_2)_m$—$OR^3$; n are independently 0, 1 or 2; m are independently 1 or 2; $R^3$ is H, $CH_3$, $CH_2CH_3$, $CH_2CH_2CH_3$ or $CH(CH_3)_2$). Furthermore, the C-acylation of keto dioxinones 42 and/or 45, or more generally 6 and/or 57, can be carried out with acylating agents to provide cannabinoids with different side chains on the aromatic ring. Examples include, but are not limited to natural side chains with $R^B$=n-propyl (cannabidivarin and tetrahydrocannabivarin families), $R^B$=n-pentyl (cannabidiol and tetrahydrocannabinol families) or unnatural side chains with $R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluorogroups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl; and o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6;

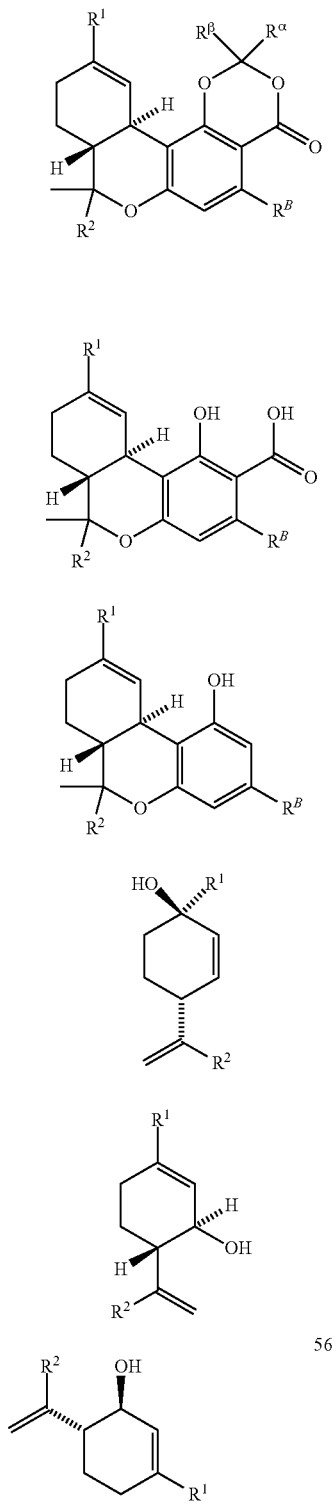

54

55

15

13

56 (enantiomer of 13)

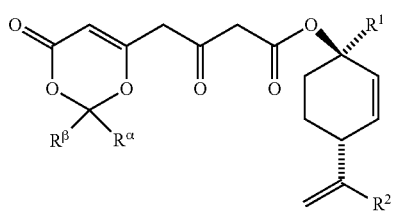

6

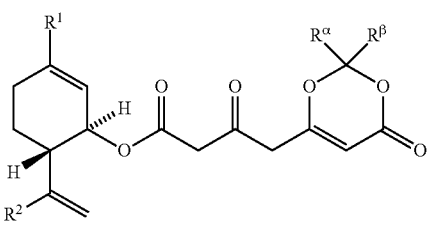

3

57 (enantiomer of 3)

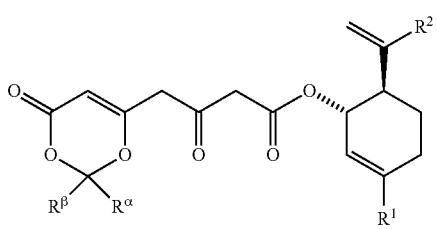

58

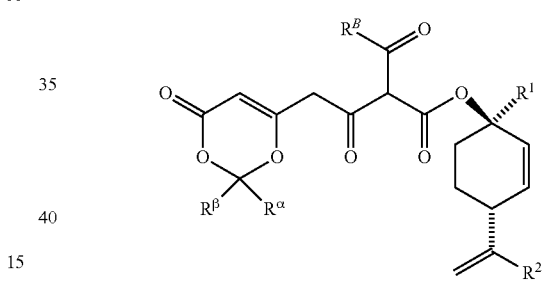

59

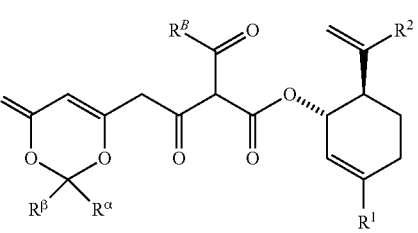

The synthetic methods in Schemes 1, 2, 3, 4 and 5 are suitable for use on a large scale and for manufacturing purposes particularly since the key cyclization reactions in the invention do not give rise to unwanted isomeric side products. Examples of known cannabinoids that are available using the synthetic routes are cannabidiol (11), cannabidivarin (12), $\Delta^9$-tetrahydrocannabinol (7), tetrahydrocannabivarin (9) and compounds related to Nabilone (16). The invention includes synthesis of the target cannabinoids as oils or crystalline derivatives, as appropriate, including solvates, hydrates and polymorphs.

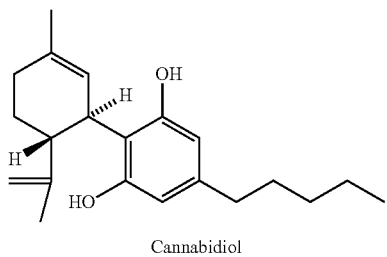
(11) Cannabidiol

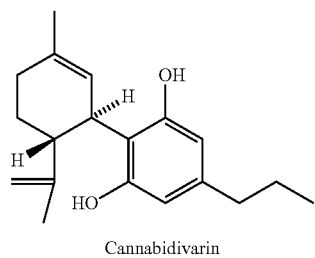
(12) Cannabidivarin

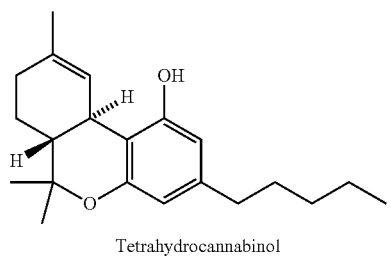
(7) Tetrahydrocannabinol

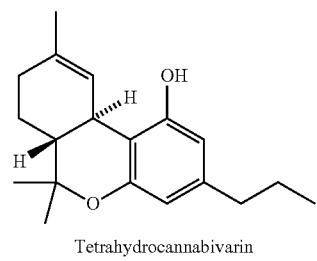
(9) Tetrahydrocannabivarin

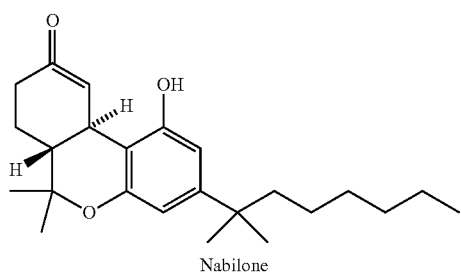
(16) Nabilone

The synthetic methods in Schemes 1, 2, 3, 4 and 5 are suitable for the synthesis of novel cannabinoids and these compounds are also part of the invention. The cannabinoids 1 below, which are novel analogs of cannabidiol (11) and cannabidivarin (12), are also available by the synthetic routes herein described and are part of the invention. The invention includes synthesis of the target cannabinoids as oils or crystalline derivatives, as appropriate, including solvates, hydrates and polymorphs. These cannabinoids 1 have the formula:

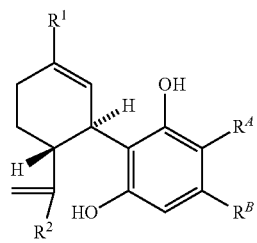
(1)

wherein:
$R^1$ is $C_2$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6.

The aforementioned novel cannabinoids with the limited formulae 1 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment or prevention of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 1 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administrated to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The cannabinoids 1 below, which are also novel analogs of cannabidiol (11), cannabidivarin (12), are also available by the synthetic routes herein described and are part of the invention. The invention includes synthesis of the target cannabinoids as oils or crystalline derivatives, as appropriate, including solvates, hydrates and polymorphs. These cannabinoids 1 have the formula:

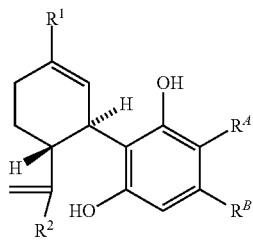

1 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is $C_2$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is H, $CO_2H$ and its pharmaceutically acceptable salts, $CO_2R^C$, $CONHR^D$, $CONR^DR^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl;

r are independently 0, 1, 2, 3, 4, 5 or 6.

The aforementioned novel cannabinoids with the limited formulae 1 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 1 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administrated to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The cannabinoids 1 below, which are novel analogs of cannabidiol (11), cannabidivarin (12), are also available by the synthetic routes herein described and are part of the invention. The invention includes synthesis of the target cannabinoids as oils or crystalline derivatives, as appropriate, including solvates, hydrates and polymorphs. These cannabinoids 1 have the formula:

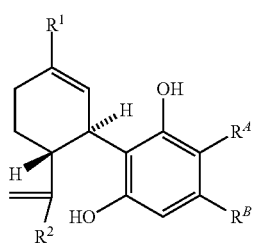

1 wherein:
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6;

The aforementioned novel cannabinoids with the limited formulae 1 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) Nabilone (16) or endocannabinoids and/or other drugs for the treatment of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 1 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administrated to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The dioxinone derivatives 3 below, which are intermediates for the synthesis of cannabinoids, are also available by the synthetic routes herein described and are part of the invention. These dioxinone derivatives 3 have the formula:

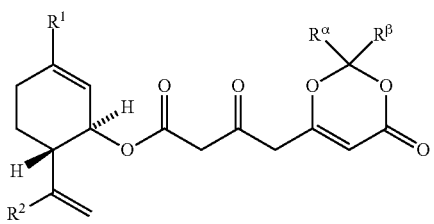

3 wherein
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is a hydroxyl protecting group, $CH_3$, $CH_2CH_3$, $CH_2CH_2CH_3$ or $CH(CH_3)_2$;
Rα and Rβ are independently $C_1$ to $C_6$ alkyl or optionally substituted aryl or Rα and Rβ in combination are $(CH_2)_s$;
s is 4, 5 or 6.

The dioxinone resorcylate derivatives 4 below, which are intermediates for the synthesis of cannabinoids, are also available by the synthetic routes herein described and are part of the invention. These dioxinone derivatives 4 have the formula:

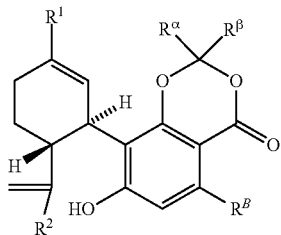

4 wherein:
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^F$ is $C_1$ to $C_6$ alkyl, $(CH_2)_r$—$C_3$ to $C_6$ cycloalkyl;
r are independently is 0, 1, 2, 3, 4, 5 or 6;
Rα and Rβ are independently $C_1$ to $C_6$ alkyl or optionally substituted aryl or Rα and Rβ in combination are $(CH_2)_s$;
s is 4, 5 or 6.

The cannabinoids 2 below, which are novel analogs of Δ⁹-tetrahydrocannabinol (7) and tetrahydrocannabivarin (9), are also available by the synthetic routes herein described and are part of the invention. The invention includes synthesis of the target cannabinoids as oils or crystalline derivatives, as appropriate, including solvates, hydrates and polymorphs. These cannabinoids 2 have the formula:

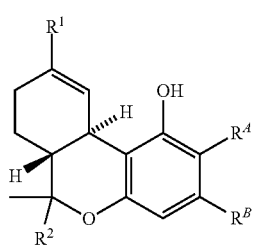

2 wherein
$R^1$ is $C_2$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6.

The aforementioned novel cannabinoids with the limited formulae 2 above may be used as active compounds either alone or admixed in combination with known cannabinoids such as but not limited to Δ⁹-tetrahydrocannabinol (7), tetrahydrocannabivarin (9), cannabidiol (11), cannabidivarin (12) Nabilone (16) or endocannabinoids and/or other drugs for the treatment of prevention of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to Δ⁹-tetrahydrocannabinol (7), tetrahydrocannabivarin (9), cannabidiol (11), cannabidivarin (12), endocannabinoids or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administered to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The cannabinoids 2 below, which are novel analogs of $\Delta^9$-tetrahydrocannabinol (7) and tetrahydrocannabivarin (9), are also available by the synthetic routes herein described and are part of the invention. The invention includes synthesis of the target cannabinoids as oils or crystalline derivatives, as appropriate, including solvates, hydrates and polymorphs. These cannabinoids 2 have the formula:

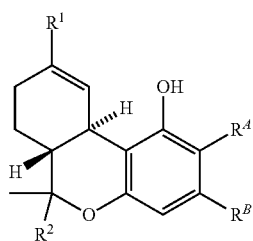

2 wherein
$R^1$ is H, $C_1$ to $C_6$ alkyl, $(CH_2)_n$—$C_3$ to $C_6$ cycloalkyl, $(CH_2)_m$—$OR^3$;
$R^2$ is $C_2$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^A$ is H, $CO_2H$ and its pharmaceutically acceptable salts, $CO_2R^C$, $CONHR^D$, $CONR^DR^E$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^C$ is $C_1$ to $C_6$ alkyl, $(CH_2)_q$—$C_3$ to $C_6$ cycloalkyl, allyl, benzyl, substituted benzyl or 2-phenylethyl;
q is 0, 1, 2, 3, 4, 5 or 6;
$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, $C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;
$R^F$ is $C_1$ to $C_6$ alkyl, $(CH_2)_r$—$C_3$ to $C_6$ cycloalkyl;
r are independently 0, 1, 2, 3, 4, 5 or 6;

The aforementioned novel cannabinoids with the limited formulae 2 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs for the treatment or prevention of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to $\Delta^9$-tetrahydrocannabinol (7), tetrahydrocannabivarin (9), cannabidiol (11), cannabidivarin (12), endocannabinoids or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administered to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The cannabinoids 2 below, which are also novel analogs of $\Delta^9$-tetrahydrocannabinol (7) and tetrahydrocannabivarin (9), are also available by the synthetic routes herein described and are part of the invention. The invention includes synthesis of the target cannabinoids as oils or crystalline derivatives, as appropriate, including solvates, hydrates and polymorphs. These cannabinoids 2 have the formula:

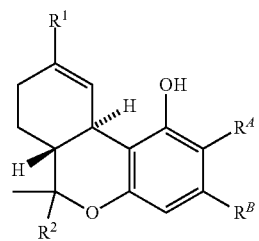

2 wherein $R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^A$ is $CONHR^D$, $CONR^DR^E$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^C$ is $C_1$ to $C_6$ alkyl, $(CH_2)_q$—$C_3$ to $C_6$ cycloalkyl, $C_3$ to $C_6$ cycloalkyl, allyl, benzyl, substituted benzyl or 2-phenylethyl;

q is 0, 1, 2, 3, 4, 5 or 6;

$R^D$ is $C_1$ to $C_6$ alkyl, $(CH_2)_r$—$C_3$ to $C_6$ cycloalkyl, allyl, benzyl, substituted benzyl or 2-phenylethyl; $R^E$ is $C_1$ to $C_6$ alkyl, $(CH_2)_r$—$C_3$ to $C_6$ cycloalkyl, allyl, benzyl, substituted benzyl or 2-phenylethyl; or $NR^DR^E$ is azetidinyl, pyrrolidinyl, morpholinyl or piperidinyl each optionally substituted by one or two hydroxyl groups or hydroxymethyl groups with the exception that the hydroxyl groups cannot be on the carbon bearing the heterocyclic ring nitrogen or the heterocyclic ring oxygen with morpholine;

$R^F$ is $C_1$ to $C_6$ alkyl, $(CH_2)_r$—$C_3$ to $C_6$ cycloalkyl.

r are independently 0, 1, 2, 3, 4, 5 or 6.

The aforementioned novel cannabinoids with the limited formulae 2 above may be used as active compounds either alone or admixed in combination with known cannabinoids such as but not limited to $\Delta^9$-tetrahydrocannabinol (7), tetrahydrocannabivarin (9), cannabidiol (11), cannabidivarin (12), endocannabinoids or Nabilone (16) and/or other drugs for the treatment or prevention of pain, multiple sclerosis-related spasticity, nausea, epilepsy, Alzheimer's brain injury/concussion, cancer, glaucoma and retinal degeneration, disorders of immune-inflammation, lung injury or disease, liver injury or disease, kidney injury or disease, eye injury or disease, amongst other pathologies. In some embodiments, the said novel cannabinoids with the limited formulae 2 above either alone or admixed in combination with known cannabinoids such as but not limited to $\Delta^9$-tetrahydrocannabinol (7), tetrahydrocannabivarin (9), cannabidiol (11), cannabidivarin (12) or Nabilone (16) and/or other drugs are formulated into pharmaceutical compositions in a suitable form for administration to a patient. Such formulations, in addition to the active cannabinoid or cannabinoids and/or other drugs in a combination therapeutic agent, contain pharmaceutically acceptable diluents and excipients, which may include binders such as lactose, starches, cellulose, sorbitol, polyethylene glycol or polyvinyl alcohol or other pharmaceutically acceptable oligosaccharides or polymers, disintegrants such as polyvinylpyrrolidone, carboxymethylcellulose or other pharmaceutically acceptable disintegrants, vehicles such as petrolatum, dimethyl sulfoxide, mineral oil, or in omega-3 oil-in-water nanoemulsions, or as complexes with cyclodextrins such as hydroxypropyl-beta-cyclodextrin, preservatives including antioxidants such as vitamin A, vitamin E, vitamin C, retinyl palmitate, cysteine, methionine, sodium citrate, citric acid, parabens or alternative pharmaceutically acceptable preservatives, antiadherents, lubricants and glidants such as magnesium stearate, stearic acid, talc, silica, pharmaceutically acceptable fats or oils, coatings such as cellulose ether hydroxypropyl methylcellulose, gelatin or other pharmaceutically acceptable coatings, and other pharmaceutically acceptable diluents or excipients. The aforementioned pharmaceutical compositions may be administrated to a patient by enteral administration for example as a pill, tablet or capsule, by sublingual administration for example as a tablet, strip, drops, spray, lozenge, effervescent tablet, intranasal administration for example as a spray or micronized powder, inhalation administration for example as a spray or micronized powder, rectal administration for example as a suppository or solution, by parenteral drug administration by intramuscular, subcutaneous or intravenous injection for example of a solution or by other known methods of clinical administration.

The dioxinone resorcylate derivatives 5 below, which are intermediates for the synthesis of cannabinoids, are also available by the synthetic routes herein described and are part of the invention. These dioxinone derivatives 5 have the formula:

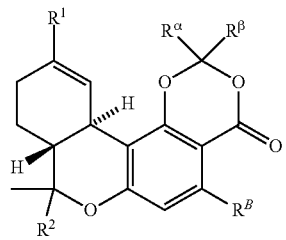

5 wherein:

$R^1$ is H, $C_1$ to $C_6$ alkyl, $(CH_2)_n$—$C_3$ to $C_6$ cycloalkyl, $(CH_2)_m$—$OR^3$;

$R^2$ is H, $C_1$ to $C_6$ alkyl, $(CH_2)_n$—$C_3$ to $C_6$ cycloalkyl, $(CH_2)_m$—$OR^3$;

n are independently 0, 1 or 2;

m are independently 1 or 2;

$R^3$ is H, $CH_3$, $CH_2CH_3$, $CH_2CH_2CH_3$ or $CH(CH_3)_2$;

$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;

o is 0, 1, 2, 3, 4, 5 or 6;

p is 1, 2, 3, 4, 5 or 6;

$R^F$ is $C_1$ to $C_6$ alkyl, $(CH_2)_n$—$C_3$ to $C_6$ cycloalkyl;

Rα and Rβ are independently $C_1$ to $C_6$ alkyl or optionally substituted aryl or Rα and Rβ in combination are $(CH_2)_s$;

s is 4, 5 or 6.

The dioxinone derivatives 6 below, which are intermediates for the synthesis of cannabinoids, are also available by the synthetic routes herein described and are part of the invention. These dioxinone derivatives 6 have the formula:

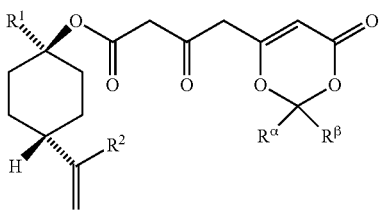

wherein
$R^1$ is H, $C_1$ to $C_6$ alkyl, $(CH_2)_n$—$C_3$ to $C_6$ cycloalkyl, $(CH_2)_m$—$OR^3$;
$R^2$ is H, $C_1$ to $C_6$ alkyl, $(CH_2)_n$—$C_3$ to $C_6$ cycloalkyl, $(CH_2)_m$—$OR^3$;
n are independently 0, 1 or 2;
m are independently 1 or 2;
$R^3$ is H, $CH_3$, $CH_2CH_3$, $CH_2CH_2CH_3$ or $CH(CH_3)_2$;
$R^B$ is H or $C_1$ to $C_2$ alkyl, linear or branched $C_3$ to $C_{10}$ alkyl or double branched $C_4$ to $C_{10}$ alkyl in each case optionally substituted by one or two hydroxyl groups or optionally substituted by one or more fluoro-groups, $(CH_2)_o$—$C_3$ to $C_6$ cycloalkyl, $(CH_2)_p$—$OR^F$, or $C_3$ to $C_6$ cycloalkyl optionally substituted by a $C_1$ to $C_8$ alkyl;
o is 0, 1, 2, 3, 4, 5 or 6;
p is 1, 2, 3, 4, 5 or 6;
$R^F$ is $C_1$ to $C_6$ alkyl, $(CH_2)_n$—$C_3$ to $C_6$ cycloalkyl;
Rα and Rβ are independently $C_1$ to $C_6$ alkyl or optionally substituted aryl or Rα and Rβ in combination are $(CH_2)_s$;
s is 4, 5 or 6.

EXAMPLES

Example 1: (1R,4R)-1-Methyl-4-(prop-1-en-2-yl)cyclohex-2-en-1-yl 4-(2,2-dimethyl-4-oxo-4H-1,3-dioxin-6-yl)-3-oxobutanoate (6, $R^1$=$R^2$=Rα=Rβ=$R^B$=$CH_3$)

N-(3-Dimethylaminopropyl)-N'-ethylcarbodiimide hydrochloride (9.6 g, 50 mmol, 1 equiv.) and 4-dimethylaminopyridine (6.0 g, 50 mmol, 1 equiv.) were sequentially added to a solution of 2-phenyl-1,3-dioxane-4,6-dione (9.6 g, 50 mmol, 1 equiv.) in anhydrous dichloromethane (0.5 L). After five minutes, 2-(2,2-dimethyl-4-oxo-4H-1,3-dioxin-6-yl)acetic acid (9.4 g, 50 mmol, 1 equiv.) was added in one portion. The reaction mixture was stirred for 17 hours at room temperature. After this period, water (0.5 L) was added and the organic fraction separated. The organic phase was washed with 1M HCl (2×0.5 L) and brine (0.5 L). The washed organic layer was dried over MgSO₄, filtered, and concentrated under reduced pressure. The crude product was immediately dissolved in anhydrous toluene (0.5 L), and (1R,4R)-1-methyl-4-(prop-1-en-2-yl)cyclohex-2-en-1-ol (4) (3.9 g, 25 mmol, 0.5 equiv.) was added as drops. The solution was heated to 55° C. and the temperature was maintained for three hours. Once the starting material had been consumed, the solution was concentrated under reduced pressure. The crude reaction product was purified by flash column chromatography (EtOAc:pentane; 2:20 to 4:20), providing the title compound as a colorless oil (4.3 g, 12 mmol, 48%): $^1$H NMR (400 MHz, CDCl₃) δ major isomer 5.46 (dq, J=8.7, 2.1 Hz, 1H), 5.40-5.30 (m, 2H), 4.78 (q, J=1.6 Hz, 1H), 4.74 (dt, J=1.9, 0.9 Hz, 1H), 3.49 (s, 2H), 3.47 (s, 2H), 2.37-2.26 (m, 1H), 2.15-2.02 (m, 1H), 2.02-1.90 (m, 1H), 1.79-1.73 (m, 2H), 1.71 (t, J=1.0 Hz, 16H), 1.70-1.66 (m, 1H); $^{13}$C NMR (101 MHz, CDCl₃) δ mixture of isomers 195.7, 166.2, 163.8, 160.6, 145.5, 140.2, 120.3, 118.8, 112.3, 111.5, 107.5, 97.2, 96.6, 92.4, 73.6, 72.4, 69.5, 61.8, 49.6, 46.9, 46.6, 44.2, 39.6, 39.5, 29.8, 26.3, 26.2, 25.1, 23.3, 19.8, 14.2; IR (neat) 2937, 1720, 1639, 1375, 1250, 1201, 1014, 901; HRMS (ES−) m/z calculated for $C_{20}H_{25}O_6$ [M−H]⁺ 361.1651, found 361.1651; $R_f$ 0.2 (EtOAc:pentane; 4:20) UV/Vanillin.

Example 2: (1R,4R)-1-Methyl-4-(prop-1-en-2-yl)cyclohex-2-en-1-yl 2-(2-(2,2-dimethyl-4-oxo-4H-1,3-dioxin-6-yl)acetyl)-3-oxooctanoate Pyridine (1.2 mL, 14 mmol, 2.0 equiv) and MgCl₂ (0.66 g, 6.9 mmol, 1.0 equiv) were added to a solution of (1R,4R)-1-methyl-4-(prop-1-en-2-yl)cyclohex-2-en-1-yl 4-(2,2-dimethyl-4-oxo-4H-1,3-dioxin-6-yl)-3-oxobutanoate (6, $R^1$=$R^2$=Rα=Rβ=$R^B$=$CH_3$) (2.5 g, 6.9 mmol, 1.0 equiv) in anhydrous dichloromethane (50 mL) cooled to 0° C. Hexanoyl chloride (1.3 g, 10 mmol, 1.5 equiv) was added dropwise, and the mixture was stirred for one hour. The cooling bath was removed and the mixture was stirred for a further two hours. Saturated aqueous NH₄Cl (50 mL) was added and the layers were separated. The aqueous layer was extracted with dichloromethane (3×50 mL). The organic extracts were washed with brine (50 mL), dried over MgSO₄, filtered, and concentrated under reduced pressure. The crude material was purified by flash column chromatography (EtOAc:pentane; 2:20) to furnish the title compound as a colorless oil (2.9 g, 6.3 mmol, 91%): NMR (400 MHz, CDCl₃) δ 5.60 (dp, J=8.6, 2.1 Hz, 1H), 5.40-5.26 (m, 2H), 4.84-4.73 (m, 2H), 3.66 (s, 2H), 2.74-2.56 (m, 2H), 2.42-2.32 (m, 2H), 2.20-1.94 (m, 3H), 1.40-1.21 (m, 7H), 0.97-0.87 (m, 5H); $^{13}$C NMR (100 MHz, CDCl₃) δ 198.4, 192.4, 166.4, 165.5, 161.0, 145.8, 140.1, 120.4, 112.3, 109.1, 107.3, 96.6, 73.2, 47.0, 42.9, 37.6, 31.7, 31.4, 29.9, 26.8, 25.9, 24.6, 23.3, 22.6, 22.4, 19.9, 14.1; IR (neat) 2933, 1732, 1702, 1639, 1390, 1375, 1271, 1202, 1068, 899, 755; HRMS (ES−) m/z calculated for $C_{26}H_{35}O_7$ [M−H]⁺ 459.2383, found 459.2390; $R_f$ 0.4 (EtOAc:pentane; 2:20) UV/Vanillin.

Example 3: 7-Hydroxy-2,2-dimethyl-8-((1R,6R)-3-methyl-6-(prop-1-en-2-yl)cyclohex-2-en-1-yl)-5-pentyl-4H-benzo[d][1,3]dioxin-4-one (4, $R^1$=$R^2$=Rα=Rβ=$R^B$=$CH_3$, $R^B$=n-$C_5H_{11}$)

Tri(2-furyl)phosphine (46 mg, 0.2 mmol, 0.2 equiv.) and tris(dibenzylideneacetone)dipalladium(0) (46 mg, 0.05 mmol, 0.05 equiv.) were sequentially added to a solution of (1R,4R)-1-methyl-4-(prop-1-en-2-yl)cyclohex-2-en-1-yl 2-(2-(2,2-dimethyl-4-oxo-4H-1,3-dioxin-6-yl)acetyl)-3-oxooctanoate (0.46 g, 1 mmol, 1 equiv.) in THF (10 mL) cooled to 0° C. The mixture was immediately allowed to warm to room temperature. After three hours, 0.5M CsOAc in iso-propanol (6 mL, 3 mmol, 3 equiv.) was added dropwise, and the reaction mixture was stirred for a further 72 hours. The reaction was quenched with 10% aqueous citric acid (10 mL), the biphasic solution was separated, and the aqueous layer was extracted with dichloromethane (3×10 mL). The organic extracts were combined and washed with brine (30 mL). The washed organic layer was dried over MgSO₄, filtered, and concentrated under reduced pressure. The crude product was purified by flash column chromatography (dichloromethane:pentane; 1:1) to provide the title compound as a white solid (128 mg, 0.32 mmol, 32%): $^1$H NMR (400 MHz, CDCl₃) δ6.45 (s, 1H), 6.41 (s, 1H), 5.48

(s, 1H), 4.57-4.51 (m, 1H), 4.41 (s, 1H), 3.91-3.82 (m, 1H), 2.99 (t, J=7.7 Hz, 2H), 2.42 (td, J=11.4, 10.9, 3.8 Hz, 1H), 2.24 (t, J=13.0 Hz, 1H), 2.11 (ddd, J=15.5, 5.1, 2.6 Hz, 1H), 1.86-1.76 (m, 4H), 1.69-1.65 (m, 5H), 1.60 (d, J=14.1 Hz, 6H), 1.34 (pd, J=6.8, 3.9 Hz, 4H), 0.88 (tq, J=7.3, 2.6, 2.1 Hz, 3H); $^{13}$C NMR (101 MHz, CDCl$_3$) δ 160.8, 156.4, 148.3, 146.4, 146.4, 123.5, 115.1, 113.9, 112.5, 104.7, 104.4, 46.4, 35.6, 34.5, 32.0, 30.6, 30.4, 28.2, 26.3, 24.9, 23.8, 22.7, 14.2; IR (neat) 3271, 2926, 1693, 1604, 1587, 1418, 1287, 1129, 1052; HRMS (ES−) m/z calculated for C$_{25}$H$_{33}$O$_4$ [M−H]$^+$ 397.2379, found 397.2386; R$_f$ 0.3 (Et$_2$O:pentane; 2:20) UV/Vanillin.

Example 4: Cannabidiol (11)

Aqueous 6 M NaOH (4 mL) was purged with nitrogen for five minutes in a sealable reaction vial. A nitrogen purged solution of 7-hydroxy-2,2-dimethyl-8-(1R,6R)-3-methyl-6-(prop-1-en-2-yl)cyclohex-2-en-1-yl)-5-pentyl-4H-benzo[d][1,3]dioxin-4-one (80 mg, 0.20 mmol) in methanol (4 mL) was added to the aqueous solution. The reaction vial was sealed and the solution was heated to 120° C. for five hours. The reaction solution was added to vigorously stirring 10% aqueous citric acid (10 mL) and Et$_2$O (10 mL). After five minutes, the layers were separated and the aqueous layer was extracted with Et$_2$O (3×10 mL). The ether extracts were washed with brine (30 mL), dried over MgSO$_4$, filtered, and concentrated under reduced pressure. The crude product was purified by flash column chromatography (Et$_2$O:pentane; 1:20 to 2:20) providing the cannabidiol (11) as an white solid (38 mg, 0.12 mmol, 60%): $^1$H NMR (400 MHz, MeOD) δ 6.07 (s, 2H), 5.28 (dq, J=2.3, 1.3 Hz, 1H), 4.49-4.39 (m, 2H), 3.96-3.88 (m, 1H), 2.90 (td, J=10.2, 5.5 Hz, 1H), 2.41-2.33 (m, 2H), 2.20 (dd, J=12.5, 6.4 Hz, 1H), 1.99 (dd, J=17.0, 3.5 Hz, 1H), 1.73 (ddd, J=8.6, 6.8, 2.8 Hz, 2H), 1.67 (dt, J=2.5, 1.1 Hz, 3H), 1.63 (t, J=1.1 Hz, 3H), 1.54 (ddd, J=14.7, 8.4, 6.7 Hz, 2H), 1.37-1.24 (m, 5H), 0.89 (t, J=7.0 Hz, 3H); $^{13}$C NMR (101 MHz, MeOD) δ 157.5, 150.3, 142.7, 134.3, 127.3, 116.0, 110.5, 108.3, 108.3, 46.4, 37.5, 36.6, 32.6, 32.0, 31.7, 30.8, 23.7, 23.6, 19.5, 14.4; R$_f$ 0.3 (Et$_2$O:pentane; 1:20) UV/KMnO$_4$.

Example 5: Δ$^9$-Tetrahydrocannabinol (7)

Cannabidiol (11) (40 mg, 0.12 mmol) in dichloromethane (1 mL) was cooled to −10° C. An ice-cooled solution of BF$_3$.2Et$_2$O in dichloromethane (1.2 mL, 0.12 mmol, 0.1 M) was added as drops over 20 minutes. The reaction mixture was stirred for a further 40 minutes at 20° C. It was diluted with diethyl ether (5 mL) and a saturated solution of NaHCO$_3$ (5 mL) was added dropwise. The layers were separated, and the aqueous fraction was extracted with diethyl ether (3 5 mL). The combined organic fractions were dried over MgSO$_4$, filtered, and concentrated under reduced pressure. The crude product was purified by flash column chromatography (5% diethyl ether in pentane) to give trans-Δ$^9$-tetrahydrocannabinol (7) tetrahydrocannabinol (31 mg, 0.99 mmol, 83%): $^1$H NMR (400 MHz, CD$_3$OD) δ 6.43 (app. pent, J=1.7 Hz, 1H), 6.16 (d, J=1.7 Hz, 1H), 6.07 (d, J=1.7 Hz, 1H), 3.15 (d, J=11.0 Hz, 1H), 2.44-2.37 (m, 2H), 2.15 (d, J=8.6 Hz, 2H), 2.00-1.91 (m, 1H), 1.66 (dq, J=2.4, 1.1 Hz, 3H), 1.60-1.24 (m, 6H), 1.37 (s, 3H), 1.05 (s, 3H), 0.90 (t, J=7.0 Hz, 4H); $^{13}$C NMR (100 MHz, CD3OD) δ 157.2, 155.8, 143.3, 133.5, 126.2, 110.4, 109.7, 108.4, 77.9, 47.5, 36.6, 35.2, 32.7, 32.3, 32.1, 28.0, 26.3, 23.6, 23.6, 19.4, 14.4; IR (neat) 3383, 2952, 2924, 2855, 1621, 1577, 1423, 1233, 1181, 1049, 1036, 835 HRMS (ES+) m/z calculated for C$_{21}$H$_{31}$O$_2$ [M−H]$^+$ 315.2319, found 315.2319; Rf 0.21 (Et$_2$O:pentane; 1:20) UV/KMnO$_4$.

Example 6: Bioassay of Synthetic Cannabidiol (11)

Figure 1B:
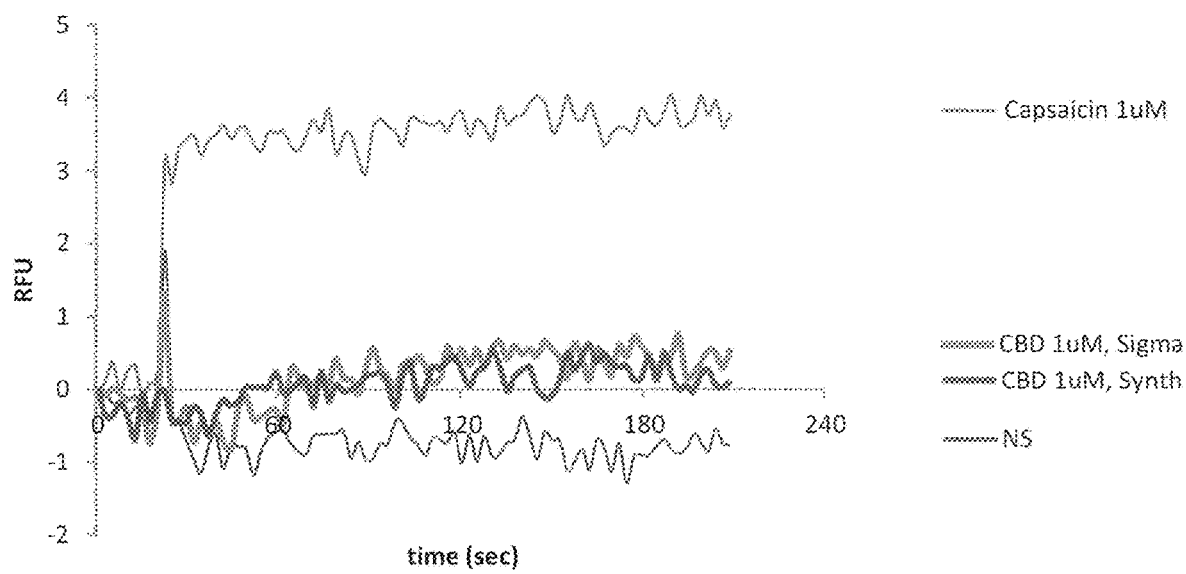
Figure 1C:
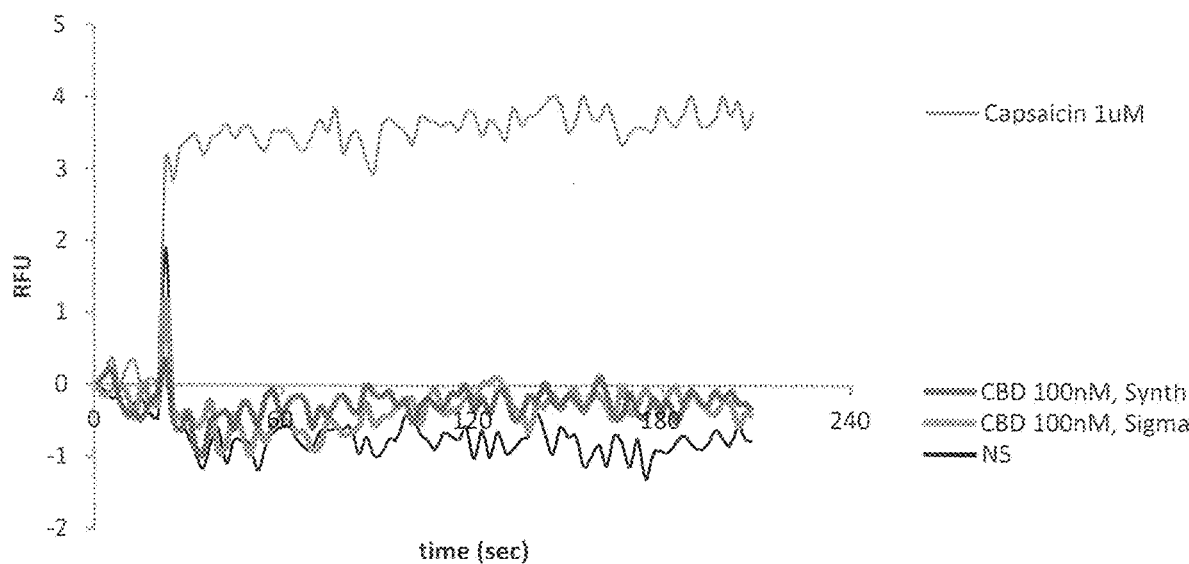
Figure 1D:
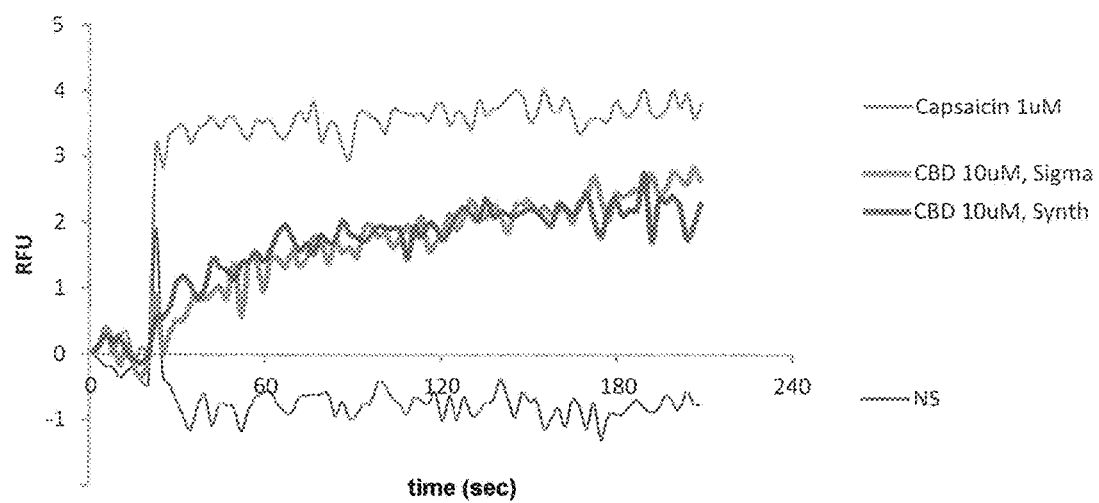

TRPV channel activity was utilized to assess and show that the biological activity of the synthesized cannabidiol (11, CBD), described herein, was the same as a reference standard cannabidiol thus further confirming the identity of the synthesized cannabidiol (11, CBD). *TRPV channels including TRPV1 have been shown to mediate effects of cannabinoids* (H. Turner, D. Chueh, T. Ortiz, A. J. Stokes and A. L. Small-Howard, Therapeutics in Parkinson's Disease: Promise and Paradox, Journal of Herbs, Spices & Medicinal Plants, 2017, volume 23, 2017, pages 231-248) and (B. Costa, G. Giagnoni, C. Franke, A. E. Trovato and M. Colleoni, Vanilloid TRPV1 receptor mediates the antihyperalgesic effect of the nonpsychoactive cannabinoid, cannabidiol, in a rat model of acute inflammation, British Journal of Pharmacology, 2004, volume 143, pages 247-250) and capsaicin, also useful as a reference standard (I. Diaz-Franulic, J. Caceres-Molina, R. V. Sepulveda, F. Gonzalez-Nilo, R. Latorre, Structure-Driven Pharmacology of Transient Receptor Potential Channel Vanilloid 1. *Molecular Pharmacology*, 2016, volume 90, pages 300-308) *HEK 293 cells with TRPV1 channels have been used as model systems* (P. Geppetti and M. Trevisani, Activation and sensitisation of the vanilloid receptor: role in gastrointestinal inflammation and function, British Journal of Pharmacology, 2004, volume 141, pages 1313-1320);

The results presented in FIGS. 1A-1D show that the sample of cannabidiol (11, CBD) synthesized by the process described herein and a reference standard cannabidiol (sourced from Sigma Aldrich) have the same "biological finger print" and dose response on TRPV 1 channels as shown using the analytical method below and as previously described (J. S. Horton, T. Shiraishi, N. Alfulait , A. L. Small-Howard, H. C. Turner, T. Kurokawa, Y. Mori and A. J Stokes, TRPV1 is a component of the atrial natriuretic signaling complex, and using orally delivered antagonists, presents a valid therapeutic target in the longitudinal reversal and treatment of cardiac hypertrophy and heart failure, Channels (Austin), 2019, volume 13, pages 1-16).

Cell Culture

HEK TRexTRPV1 cultured in DMEM, 10% Fetal Bovine Serum, 2 mM L-glutamine, 10 microgramg/ml Blasticidin (Calbiochem, San Diego Calif.), 400 mg/ml Zeocin (InvivoGen, San Diego Calif.), followed by inducing indicated transgene expression using 1 microgram/ml Tetracycline for 16-24 hrs. Comparisons made to untransfected HEK cells or HEKTRexTRPV1 with or without induction.

Calcium Assay

Cells washed and incubated with 0.2 micromolar Fluo-4 [54] for 30 minutes at 37° C. in a standard modified Ringer's solution of the following composition (in mM): NaCl 145, KCl 2.8, CsCl 10, CaCl$_2$ 10, MgCl$_2$ 2, glucose 10, Hepes.NaOH 10, pH 7.4, 330 mOsm. Cells transferred to 96-well plates at 50,000 cells/well and stimulated as indicated. Calcium signals acquired using a Flexstation 3 (Molecular Devices, Sunnydale, USA). Data are analyzed according to the methods in I. Diaz-Franulic, J. Caceres-Molina, R. V. Sepulveda, F. Gonzalez-Nilo, R. Latorre, Structure-Driven Pharmacology of Transient Receptor Potential Channel Vanilloid 1, *Molecular Pharmacology,* 2016, volume 90, pages 300-8.

Dose response and comparison in HEK-TRPV1 cells between the Cannabidiol (11, CBD) synthesized according to the described method (identified in FIGS. 1A-1D as "CBD, Synth") to Sigma-sourced CBD (CAS No. 13956-29-1, identified in FIGS. 1A-1D as "CBD, Sigma") is depicted in FIGS. 1A-1D. Normal saline reference standard is identified as "NS" in FIGS. 1A-1D.

All samples tested under the identical conditions: Fluo-4 loaded cells in 1 mM external calcium chloride; 0-20 seconds baseline; at 20 seconds, compound added. (uM=micromolar).

What is claimed is:

1. A compound having a structure of one of formulae 3 or 6:

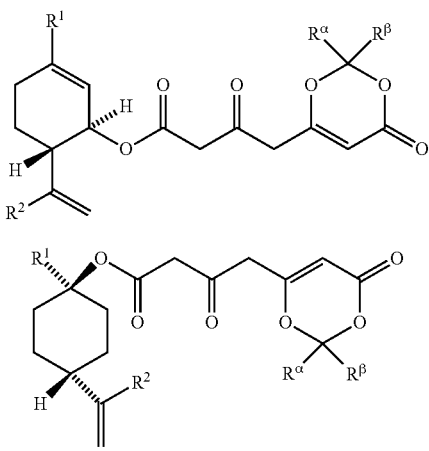

wherein:
$R^1$ is selected from a group consisting of H, $C_1$ to $C_6$ alkyl, $(CH_2)_n$—$C_3$ to $C_6$ cycloalkyl, and $(CH_2)_m$—$OR^3$;
$R^2$ is selected from a group consisting of H, $C_1$ to $C_6$ alkyl, $(CH_2)_n$—$C_3$ to $C_6$ cycloalkyl, and $(CH_2)_m$—$OR^3$; wherein
each n is independently 0, 1 or 2;
each m is independently 1 or 2;
$R^3$ is selected from a group consisting of H, $CH_3$, $CH_2CH_3$, $CH_2CH_2CH_3$, and $CH(CH_3)_2$;
Rα and Rβ are independently $C_1$ to $C_6$ alkyl or optionally substituted aryl, or
Rα and Rβ in combination are $(CH_2)_s$; wherein
s is 4, 5 or 6.

2. The compound of claim 1, wherein Rα and Rβ are both $CH_3$.

3. The compound of claim 2, wherein $R^1$ and $R^2$ are $CH_3$.

4. The compound of claim 2, wherein the compound is a single enantiomer.

5. The compound of claim 2, wherein the compound is a racemic mixture of enantiomers.

6. The compound of claim 2, wherein the compound is a mixture of enantiomers in non-equal proportions.

7. The compound of claim 1, wherein the compound is a single enantiomer.

8. The compound of claim 1, wherein the compound is a racemic mixture of enantiomers.

9. The compound of claim 1, wherein the compound is a mixture of enantiomers in non-equal proportions.

10. The compound of claim 1, wherein the compound has the structure of formula 3.

11. The compound of claim 2, wherein the compound has the structure of formula 3.

12. The compound of claim 3, wherein the compound has the structure of formula 3.

13. The compound of claim 4, wherein the compound has the structure of formula 3.

14. The compound of claim 5, wherein the compound has the structure of formula 3.

15. The compound of claim 1, wherein the compound has the structure of formula 6.

16. The compound of claim 2, wherein the compound has the structure of formula 6.

17. The compound of claim 3, wherein the compound has the structure of formula 6.

18. The compound of claim 4, wherein the compound has the structure of formula 6.

19. The compound of claim 5, wherein the compound has the structure of formula 6.

* * * * *

UNITED STATES PATENT AND TRADEMARK OFFICE
CERTIFICATE OF CORRECTION

PATENT NO. : 11,685,724 B2
APPLICATION NO. : 17/738055
DATED : June 27, 2023
INVENTOR(S) : Barry A. Berkowitz, Anthony G. Barrett and Daniel Elliott Page 1 of 1

It is certified that error appears in the above-identified patent and that said Letters Patent is hereby corrected as shown below:

In the Claims

Claim 1, Column 61, Lines 25-32:

Delete " 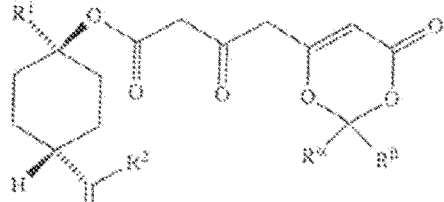 "

And insert -- 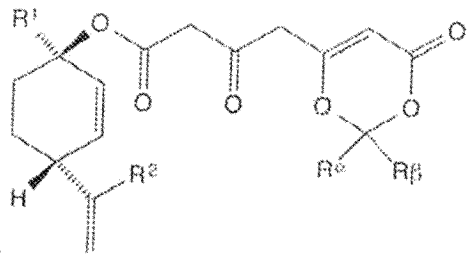 --

Signed and Sealed this
Fifth Day of September, 2023

Katherine Kelly Vidal
Director of the United States Patent and Trademark Office